(12) United States Patent
Cho et al.

(10) Patent No.: US 7,147,373 B2
(45) Date of Patent: Dec. 12, 2006

(54) METHOD AND SYSTEM FOR CALIBRATING A SOURCE AND DETECTOR INSTRUMENT

(75) Inventors: Young-bin Cho, Mississauga (CA);
Douglas J. Moseley, Aurora (CA);
Jeffrey H. Siewerdsen, Toronto (CA);
David A. Jaffray, Etobicoke (CA)

(73) Assignee: University Health Network, Toronto (CA)

( * ) Notice: Subject to any disclaimer, the term of this patent is extended or adjusted under 35 U.S.C. 154(b) by 0 days.

(21) Appl. No.: 10/915,015

(22) Filed: Aug. 9, 2004

(65) Prior Publication Data

US 2005/0117708 A1 Jun. 2, 2005

Related U.S. Application Data

(60) Provisional application No. 60/493,953, filed on Aug. 8, 2003.

(51) Int. Cl.
 *G01D 18/00* (2006.01)
 *H05G 1/28* (2006.01)

(52) U.S. Cl. .................. 378/207; 378/20; 378/164
(58) Field of Classification Search ............ 378/20, 378/164, 207, 18, 163, 205, 901; 250/363.09, 250/370.1
See application file for complete search history.

(56) References Cited

U.S. PATENT DOCUMENTS

| | | | |
|---|---|---|---|
| 4,194,292 A * | 3/1980 | Wojcik .................. | 33/30.2 |
| 5,442,674 A | 8/1995 | Picard et al. | |
| 5,835,561 A | 11/1998 | Moorman et al. | |
| 6,044,132 A * | 3/2000 | Navab .................. | 378/163 |
| 6,206,566 B1 * | 3/2001 | Schuetz .................. | 378/205 |
| 6,776,526 B1 * | 8/2004 | Zeiss .................. | 378/207 |
| 2002/0085668 A1 * | 7/2002 | Blumhofer et al. ........... | 378/68 |
| 2002/0131559 A1 | 9/2002 | Launay et al. | |
| 2003/0058999 A1 | 3/2003 | Mitschke et al. | |
| 2004/0252811 A1 * | 12/2004 | Morita et al. ............ | 378/207 |

FOREIGN PATENT DOCUMENTS

JP 2005021675 A * 1/2005
WO WO 03/020114 A2 3/2003

* cited by examiner

*Primary Examiner*—Edward J. Glick
*Assistant Examiner*—Anastasia S. Midkiff
(74) *Attorney, Agent, or Firm*—Lahive & Cockfield, LLP

(57) ABSTRACT

A system for obtaining coordinate data of a source and detector instrument are described. The system includes a marker assembly having a plurality of markers with a particular geometry, and an energy source for targeting the plurality of markers with energy packets. The system further includes a detector for detecting energy packets after the plurality of markers have interacted therewith, and an image device for forming image data of the plurality of markers from the energy packets detected by the detector. A calibration module for utilizes the particular geometry of the plurality of markers and the image data to non-iteratively determine coordinate data.

22 Claims, 23 Drawing Sheets

(a)

PLASTIC TUBE OF
CALIBRATION PHANTOM (b)

METHOD AND SYSTEM FOR CALIBRATING A SOURCE AND DETECTOR INSTRUMENT

CROSS-REFERENCE TO RELATED APPLICATION

The instant application claims priority to Provisional Application No. 60/493,953, filed Aug. 8, 2003, whose contents are incorporated herein by reference.

FIELD OF THE INVENTION

The invention relates to source and detector instruments, and more specifically to calibrating such instruments.

BACKGROUND OF THE INVENTION

Volumetric imaging has become an integral part of modern medicine. Such imaging has been widely used to not only diagnose disease but as an aid in administering medical treatments. When using diagnostic probes, operating instruments or radiation therapy, a medical professional can be greatly aided by images taken of the patient that can identify target areas, or areas to be avoided.

For example, cone-beam computed tomography (CBCT) instruments have been coupled to X-ray delivery devices to provide in situ clinical imaging and radiation therapy simultaneously. The Elekta Synergy™ system is an example of a commercially available system that combines imaging and delivery into one integrated treatment system for precise delivery of radiation therapy.

Although the integration of imaging systems with delivery systems has many advantages, there is at least one drawback. Both imaging systems and delivery systems have components that move, typically in a circular motion. When imaging and delivery systems are integrated, motion of the components is less stable than the separate systems, resulting in perturbations from ideal behavior.

Such perturbations denigrate performance. For example, in cone beam tomography, non-ideal motion, such as tilting or twisting of the image device, can produce severe artifacts, such as loss of detail, poor registration, and streak artifacts. In the delivery system, perturbations can cause inaccurate delivery of energy to a part of the body. Therefore, any system or method that can account for non-ideal motion would be most welcome.

SUMMARY OF THE INVENTION

This invention is directed to a method and apparatus for obtaining coordinate data of a source and detector system in one configuration captured by one imaging view, or "pose." A source and detector system includes a source of material or wave energy that interacts with a target, and a detector for obtaining image data of the target. Source and detector systems include imaging and treatment delivery systems, and systems combining both.

In one embodiment, the invention employs a device (referred to as a marker assembly) containing a plurality of fiducial markers that are visible in a projection image. Coordinate data associated with a particular pose of the projection system are then computed. The coordinate data can include position and orientation coordinates of the detector, and position coordinates of the source, which if considered to be a point source, is devoid of orientation. The method makes use of analytical expressions relating image data to the known geometry of the plurality of markers to non-iteratively obtain the coordinate data associated with a pose.

The technique is general to source and detector systems, including systems where the energy source is an X-ray source, a gamma ray source, an atomic/sub-atomic particle source, an optical photon source, or other non-diffracting energy source. It allows determination of pose from a single projection and may be used to determine pose throughout an arbitrary trajectory of source and detector in which multiple projections are formed—e.g., the source and detector moving in linear or circular trajectories. Applications in medical imaging in which the invention may be applied include single or multiple view radiography, stereography, bi-plane imaging, fluoroscopy, tomosynthesis, and cone-beam computed tomography. Example sources in medicine include x-ray tubes, linear accelerators, and radionuclides. Example detectors in medical imaging include film, computed radiography storage phosphors, x-ray image intensifiers, and flat-panel detectors.

A direct, non-iterative method is provided herein for determination of pose based on the position of the fiducial markers in a given projection image. The location of markers within the phantom are known with respect to one another. The phantom may be placed arbitrarily with respect to source and detector provided that the fiducial markers are visible in the projection image. A specific embodiment of the invention involves a phantom containing markers, such as metal ball bearings, arranged in two circles, which project as ellipses. By relating the known geometries of the markers and their projection, the location $(X_s, Y_s, Z_s)$ of the source as well as the location $(X_d, Y_d, Z_d)$ and orientation $(\theta, \phi, \eta)$ of the detector may be ascertained using a direct, non-iterative analysis. This analysis is fast, accurate, and general in that it can completely determine pose from a single projection, allowing complete specification of system geometry for a system in which a single projection is acquired and/or for a system in which the source and detector move in some trajectory about the phantom and acquire one or multiple projections. The resulting pose(s) is completely specified in the reference frame of the phantom, which can in turn be related to other reference frames by appropriate transformations, such as the reference frame of a medical treatment device or any other system utilizing data from the projection system.

BRIEF DESCRIPTION OF THE DRAWINGS

For a better understanding of the present invention and to show more clearly how it may be carried into effect, reference will now be made, by way of example, to the accompanying drawings.

DETAILED DESCRIPTION OF THE INVENTION

Figure 1:
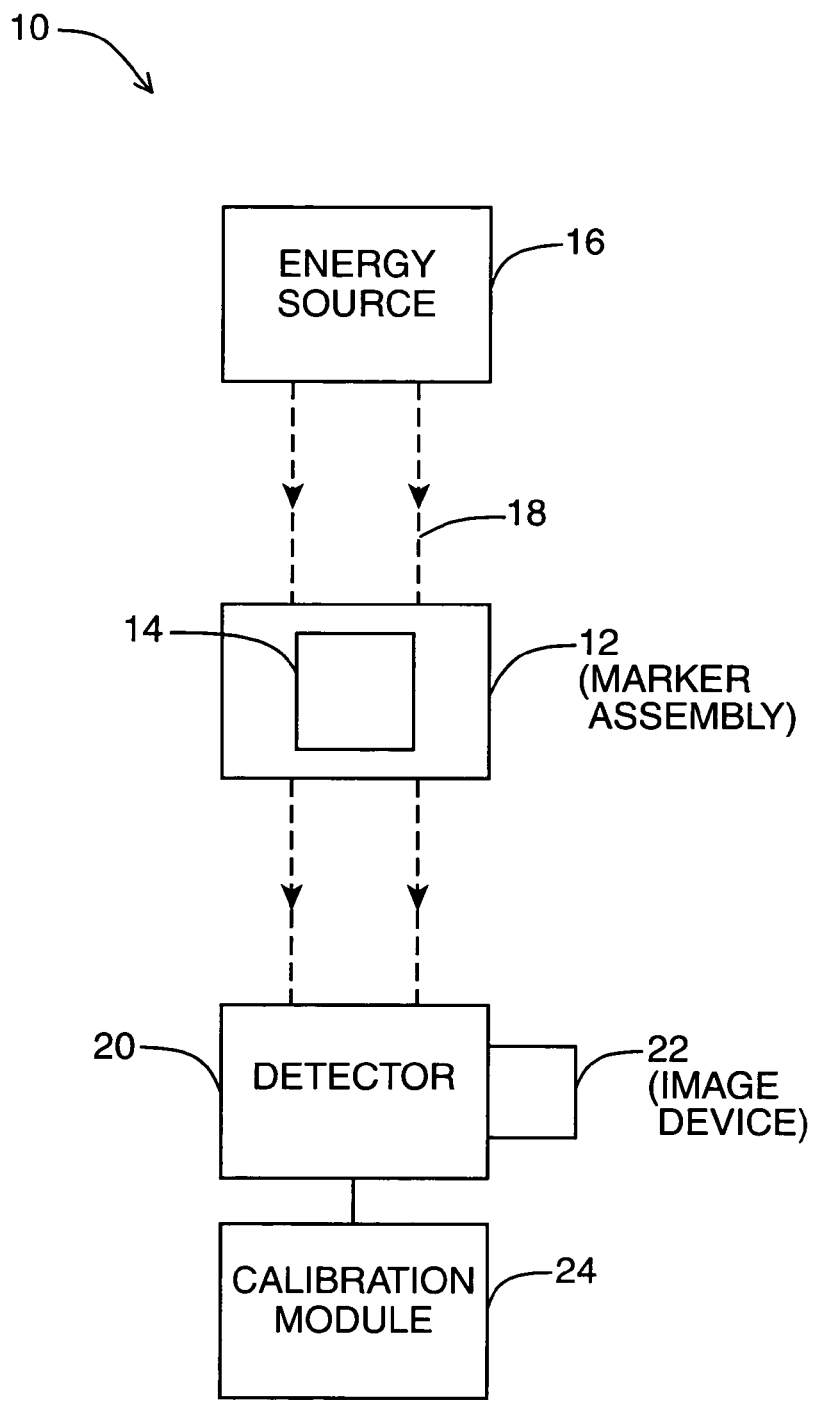
FIG. 1 shows a box-diagram of a calibration system for calibrating an imaging instrument according to the principles of the present invention.

FIG. 1 shows a box-diagram of a calibration system 10 for calibrating a source and detector instrument. For example, the source and detector instrument can be an imaging instrument used to image a body part, such as a radiography, a stereography, a bi-plane imaging, a fluoroscopy, a tomosynthesis or a tomography instrument.

The calibration system 10 includes a "phantom" or marker assembly 12 having a plurality of markers 14 whose locations with respect to one another is known. The calibration system 10 further includes an energy source 16 that can emit energy packets 18, a detector 20, an image device 22, and a calibration module 24.

The energy source 16 targets the plurality of markers 14 with energy packets 18. The energy source 16 can include an x-ray, a gamma ray, an atomic, a sub-atomic, an optical photon, an electromagnetic wave, an x-ray tube, a particle accelerator or a radionuclide source.

The detector 20 detects energy packets after the plurality of markers have interacted therewith. The image device 22 forms image data of the plurality of markers 14 from the energy packets detected by the detector 20.

As described in more detail below, the calibration module 24 utilizes the locations of the plurality of markers 14 and the image data to non-iteratively determine coordinate data of at least one of the energy source 16 and the detector 20. The coordinate data allow the imaging instrument to be calibrated. Calibration of a system allows images of a subject to be properly evaluated.

FIGS. 2A–E shows the marker assembly 12 of FIG. 1. The marker assembly 12 includes a cylindrical plastic phantom 32 having end caps 33. The marker assembly 12 also includes a plurality of markers 14 embedded in the phantom 32. The plurality of markers 14, in this case twelve steel ball bearings (BBs), are disposed on two parallel circles at opposite ends of a cylinder of radius r and length l. The first circle 34 and the second circle 36 each have a radius of r=50 mm. The twelve BBs on each circle 34 and 36 are equally spaced to within a 25 µm tolerance. The diameter of each ball bearing is 4.7 mm, and the distance between the two circles 34, 36 is 160 mm. It should be understood that in other embodiments the plurality of markers 14 can take on other shapes and sizes, and can be arranged in a different geometry.

After being emitted from the energy source 16, the energy packets 18 interact with the BBs 14 and then are detected by the detector 20. The image device 22 forms image data of the BBs 14 from the energy packets detected. As described in more detail below, the image data may correspond, for example, to a radiographic image of a first ellipse associated with a first projection of the first circle 34 and a second ellipse associated with a second projection of the second circle 36.

To create a relatively uniform background around the BBs in the radiographic image, and to protect the BBs from mechanical damage, a plastic end cap 33 is provided at each end of the cylindrical plastic phantom 32.

The phantom 32 is large enough to ensure that most of the detector 20 is involved in forming the image. In addition, the diameter of each BB is large enough to include a large number of pixels and to exhibit high contrast, yet small enough to avoid overlapping with neighboring BBs when projected to form an image. Preferably, more than ten BBs (five in each circle) should be used in the marker assembly 12 to best employ ellipse parameters associated with the first and second ellipses, which are described below with reference to equation (8).

Figure 2:
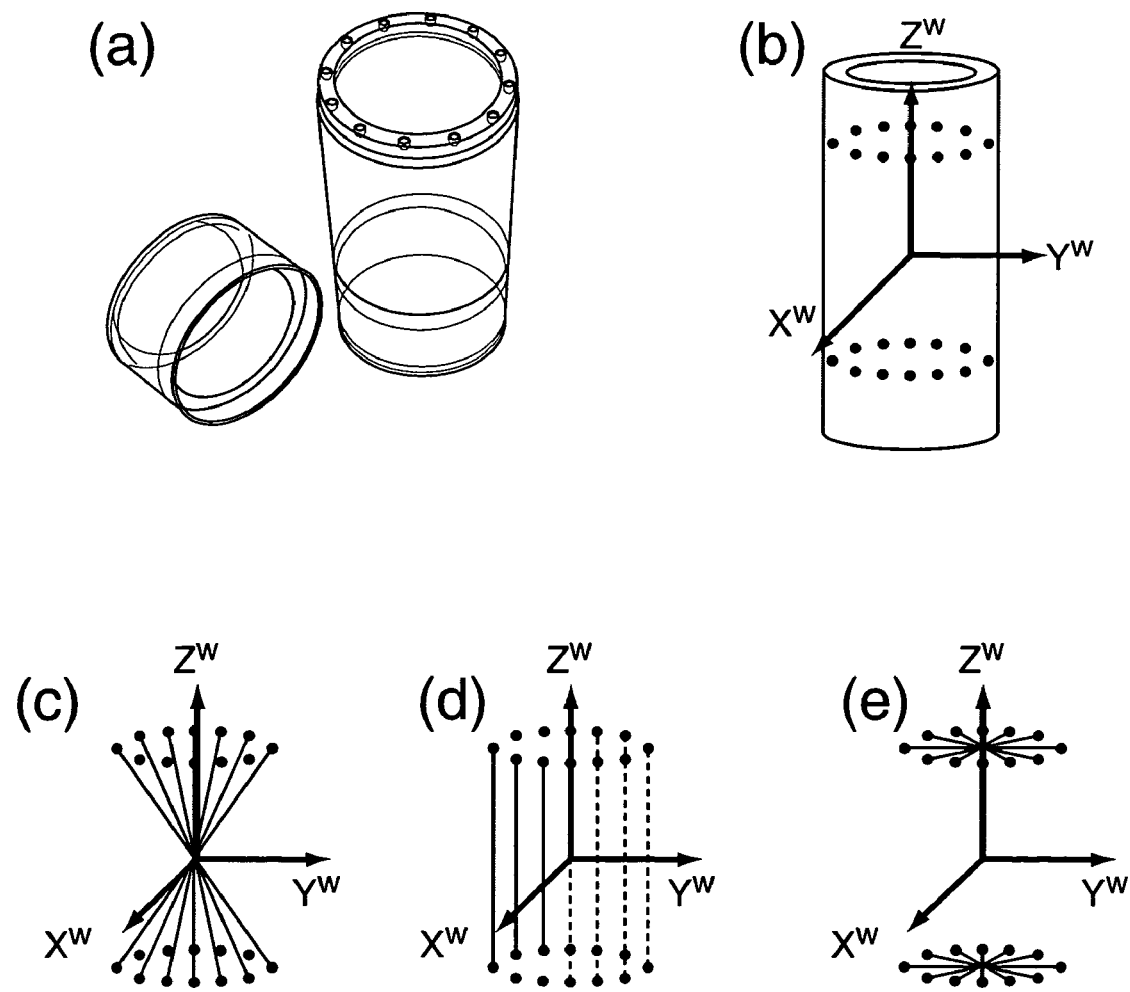
FIGS. 2A–E show the marker assembly of FIG. 1.

The arrangement of BBs in the marker assembly 12 possesses a degree of symmetry that facilitates the subsequent calibration analysis. In particular, the BBs can be divided into groups of four ball bearings such that the positions of the BBs are (x, y, z), (−x, −y, z), (x, y, −z), and (−x, −y, −z) with respect to a particular set of coordinates axes, the phantom coordinate system. The origin of the phantom coordinate system is the point of intersection of the lines connecting the BBs in FIG. 2C. The z-axis of the phantom coordinate system is parallel to the lines connecting the BBs in FIG. 2D. Having more than two groups of BBs allows the center of each circular pattern to be found, as shown in FIG. 2E. Since each group consists of four BBs, at least 12 ball BBs are used.

Figure 3:
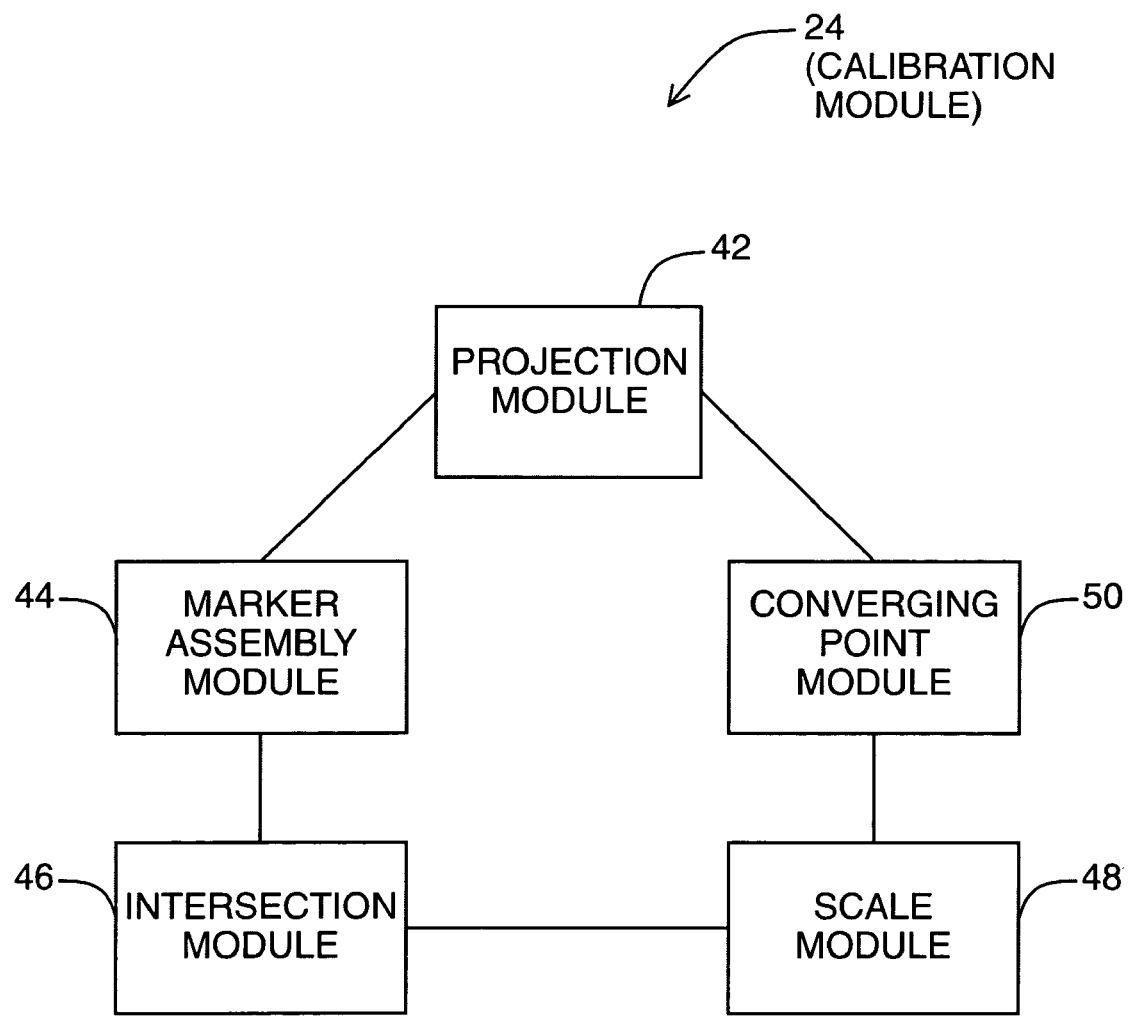
FIG. 3 shows the calibration module of FIG. 1.

FIG. 3 shows the calibration module 24 of FIG. 1. The calibration module 24 includes a projection module 42, a marker assembly module 44, an intersection module 46, a scale module 48, and a converging point module 50. These modules 42, 44, 46, 48 and 50 obtain data from which coordinate data of the energy source 16 and detector 20 may be calculated.

In particular, the projection module 42 obtains first ellipse parameters $a_1, b_1, c_1, u_{01}, v_{01}$ that describe the first ellipse, which is the image projection of the first circle 34, and second ellipse parameters $a_2, b_2, c_2, u_{02}, v_{02}$ that describe the second ellipse, which is the image projection of the second circle 36, according to $$a(u-u_0)^2 + b(v-v_0)^2 + 2c(u-u_0)(v-v_0) = 1$$

where $(u_o, v_o)$ is the center of the ellipse. The parameters $a, b, c, u_0$ and $v_0$ can be found using a linear least square method from projection points of the BBs.

The marker assembly module 44 stores geometric parameters of the marker assembly 12, such as the radius, r, of, and distance, l, between the first and second circles 34 and 36.

The intersection module 46 determines a location of a piercing or intersection point, $(U_{offset}, V_{offset})$ defined as follows. Each member of the plurality of markers 14 on the first circle 34 has a counterpart on the second circle 36, viz., the member of the plurality of markers 14 on the second circle 36 farthest away. Lines connecting members of the plurality of markers 14 to their counterpart on the second circle 36 intersect at a point that coincides with the origin of the phantom coordinate system (see FIG. 2C). A BB placed at this point would form an image, as obtained by the imaging instrument, which by definition is the piercing point. In reality, no such BB is placed there. Instead, the piercing point may be obtained by connecting with lines the images of BBs on the first and second circles 34 and 36 (which project generally as ellipses) with their counterpart images; where the lines intersect is the piercing point.

To locate the position of the BBs on the image, a signal threshold is chosen such that the edge of each ball bearing is shown clearly. A numerical optimization package, such as fminsearch from Matlab™ (the MathWorks, Natick, Mass.), is used to find the center of each ball bearing.

The scale module 48 obtains a scale factor, $S_f$, having dimensions of pixel/length. The scale factor can be used to digitize the image of the plurality of markers 14 according to equations (7A) and (7B) below.

Figure 4:
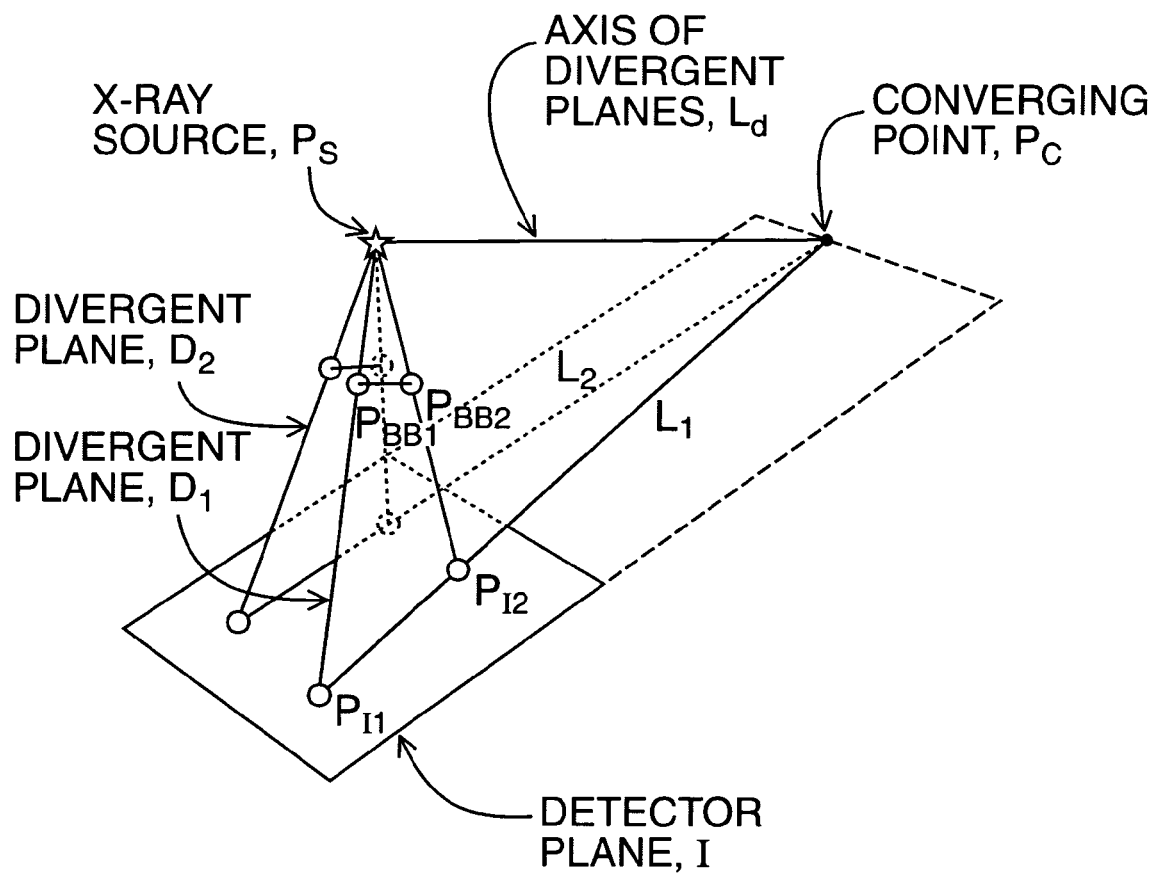
FIG. 4 illustrates the concept of a converging point used to obtain coordinate data according to the principles of the present invention.

The converging point module 50 obtains the converging point, defined as follows. Referring to FIG. 4, one source $(P_s)$ and two point objects $(P_{BB1}$ and $P_{BB2})$ define a plane, called a divergent plane, $D_1$. The intersection of the divergent plane, $D_1$, and the detector plane, I, is the line, which connects the projected BB locations $(P_{I1}$ and $P_{I2})$. Another pair of BBs forms another divergent plane in the same way.

$$L_i = I \cap D_i$$

where $D_i$ is i-th divergent plane, and $L_i$ is the line made by $I \cap D_i$. The intersection of all lines $(L_i)$ is denoted by the converging point, $P_c$:

$$P_c = L_1 \cap L_2 \cap L_3 \cap \ldots$$
$$= (I \cap D_1) \cap (I \cap D_2) \cap \ldots$$
$$= I \cap (D_1 \cap D_2 \cap \ldots)$$

If all the lines connecting a pair of point objects are parallel, the intersection of divergent planes, $(D_1 \cap D_2 \cap \ldots)$, forms one line, $L_d$, denoted by the axis of the divergent planes, which is parallel to the lines. The converging point, $P_c$, always exists on the (extended) detector plane except for the special case where the axis of divergent planes is parallel to the detector plane. The divergent planes and the axis of the divergent planes are analogous to sheets of paper and the spine of a book. Therefore, the converging point is simply calculated as follows.

$$P_c = I \cap L_d$$

When more than two pairs of point object are available, and the lines connecting a pair of objects in the space are parallel, the converging points formed by the lines connecting pairs of objects in the image can be simply found by the intersection of the axis of the divergent plane, $L_d$, and the detector plane, I.

From the ellipse parameters obtained by the projection module 42, the geometric parameters of the marker assembly 12 obtained by the marker assembly module 44, the piercing point obtained by the intersection module 46, the scale factor obtained by the scale module 48, and particular converging points obtained by the converging point module 50, coordinate data of the energy source 16 and detector 20 may be obtained. In particular, the calibration module 24 determines the coordinate data, which can include three detector orientation coordinates, $(\theta, \phi, \eta)$ (or pitch, roll, yaw), defining an orientation of the detector, three detector position coordinates, $(X_d, Y_d, Z_d)$ defining a position of the detector, and three source coordinates, $(X_s, Y_s, Z_s)$, defining a position of the energy source.

These coordinate data are obtained non-iteratively, meaning that equations, which are provided below, are used that relate the unknown coordinate data to known quantities, such as the ellipse parameters found by the projection module 42 and the geometric parameters of the phantom 32. Specifically, $\eta_d$ is obtained from equation (16), $\theta_d$ and $\phi_d$ from equations (9), (10), (18), and (19), $Y_d$ and $Z_d$ from equations (24) and (23), and $Y_s$ and $Z_s$ from equations (15) and (17). Positions $X_d$ and $X_s$ are zero by construction.

This non-iterative approach should be contrasted with iterative approaches where an initial guess is made of coordinate data that might yield the image obtained. A determination of what type of image would result from the guessed coordinate data is then made, followed by a sequence of other guesses and image determinations. The hope is that the sequence of guesses converges to one that more or less yields the experimentally determined image. Non-iterative methods can be more advantageous than iterative approaches because they can be done more quickly, and because they don't suffer from non-convergence problems.

Figure 5:
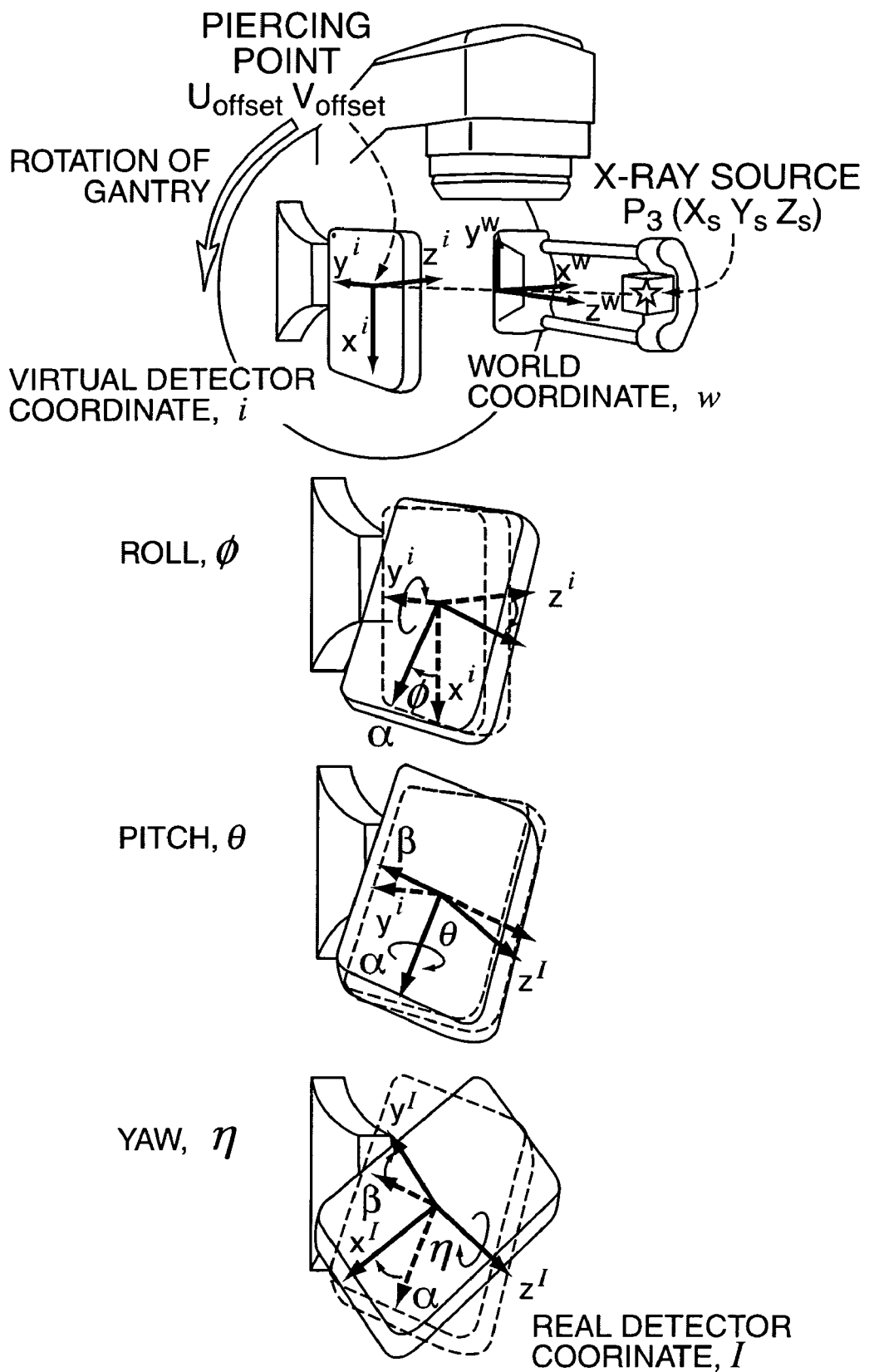
FIG. 5 shows coordinate systems used to calibrate a gantry-based, imaging instrument according to the principles of the present invention.
Figure 6:
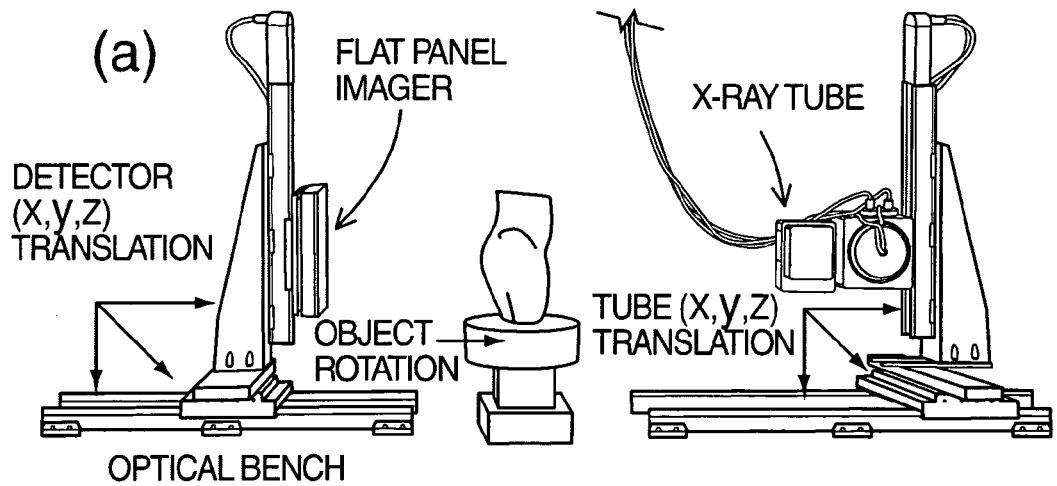
FIGS. 6A and 6B show coordinate systems used to calibrate a bench-top, turntable imaging instrument according to the principles of the present invention.
Figure 6:
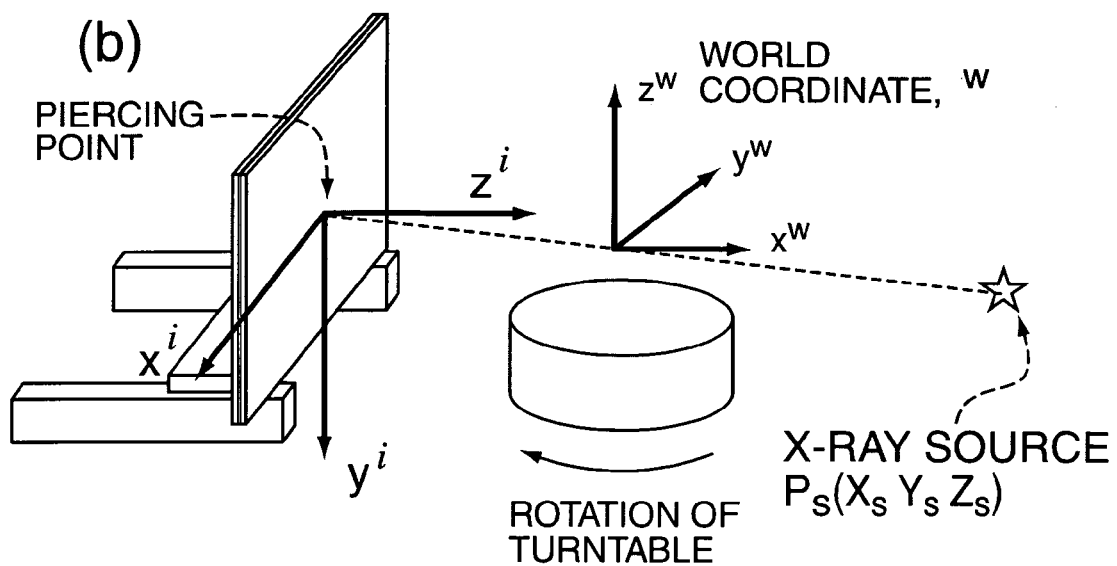

To derive the aforementioned equations and other intermediate equations for deriving the coordinate data of the imaging instrument, three right-handed Cartesian coordinate systems are introduced: a world (w) coordinate system, virtual detector (i) coordinate system, and real detector (l) coordinate system, which are shown in FIGS. 5 and 6A–B. The phantom 32, and the patient are fixed with respect to the world coordinate system. In FIG. 5, a medical linear accelerator/CT imaging instrument having a rotating gantry is shown. In the embodiment shown, a medical linear accelerator, used for the therapeutic delivery of energy packets, is integrated with a cone-beam computer tomography (CT) imaging system. For this type of instrument, the world coordinate system is fixed in space. For an instrument composed of a rotating turntable and cone-beam computerized tomography laboratory bench, shown in FIGS. 6A–B, the world coordinate system is fixed to the rotating table. The z-axis of the world coordinate system $(z^w)$, is along the rotation axis of the gantry for the medical linear accelerator/CT imaging instrument, and along that of the turntable for the laboratory bench instrument. The $x^w$ axis points to the source at a gantry angle of zero and $y^w$ points to the source at a gantry angle of 90° degrees. The positive direction of rotation of the turntable ($-z^w$) is opposite to that of the gantry ($z^w$). Under this convention, the source appears to move around from the x-axis ($x^w$) to y-axis ($y^w$) in both the fixed and rotating world coordinate systems, when the gantry or turntable rotates from 0 degree to 90 degrees. The laboratory cone-beam CT system can be adjusted through three axes of linear motion for the x-ray source and detector, along with one rotation axis and one linear axis for the phantom 32 and turntable. The resolution of the computer controlled positioning system is 30 μm in all directions and 0.015° in rotation.

The origin of the virtual detector system is located at the projection point of the origin of the world coordinate system on the detector plane. This point is also the piercing point. The y-axis of the virtual detector coordinate system is anti-parallel to the z-axis of world coordinate system. The direction of the $x^i$ axis is oriented perpendicular to the vector from the piercing point to the source point and the y-axis of the virtual detector. The real detector system is used to model possible tilting, specified by a roll angle $\phi$ and a pitch angle $\theta$, and rotation, specified by a rotation angle $\eta$ about the detector normal axis of the detector from the virtual detector plane as shown in FIG. 5.

Once the coordinate systems are defined, objects in one coordinate system can be easily referenced to another. The following equation expresses the transformation of a position vector ($P^w$) in the world coordinate system to one ($P^i$) in the virtual coordinate system.

$$P^i = R^i_w P^w + T^i_w \qquad (1)$$

where $P \in R^{3 \times 1}$, $R^i_w \in R^{3 \times 3}$, and $T^i_w \in R^{3 \times 1}$ are position of object, rotation matrix and translation vector, respectively. The rotation matrix, $R^i_w$ and translation vector, $T^i_w$ can be written as follows.

$$R^i_w = \begin{bmatrix} St & Ct & 0 \\ 0 & 0 & -1 \\ -Ct & St & 0 \end{bmatrix} \qquad (2)$$

and $$T^i_w = [X_d \ Y_d \ Z_d] \qquad (3)$$

where St and Ct are sine and cosine of the nominal gantry angle, t. The translation vector, $T^i_w$, is the position vector from the origin of i to the origin of w. The subscript d is used to indicate the position of detector. Since the virtual detector system is defined such that piercing point is perpendicular to the $x^i$, $X_d$ is zero and the x-ray source appears in the y-z plane of the virtual detector coordinate system. Therefore, calibration parameters in this transformation are t, $Y_d$, and $Z_d$. Detector rotation and/or tilting information are included in the rotation matrix, $R^l_i$. This matrix transforms vectors from the virtual detector system (i) to the real detector system (l) according to $$P^l = R^l_i P^i \qquad (4)$$

where $P^l = [X^l \ Y^l \ Z^l]^T$ and $P^i = [X^i \ Y^i \ Z^i]^T$ are position vectors in the real detector and virtual detector systems, respectively. $R^l_i$ can be written as follows using the parameters, $\phi$, $\theta$, and $\eta$:

$$R^l_i = \begin{bmatrix} C\phi C\eta - S\theta S\phi S\eta & C\theta S\eta & -S\phi C\eta - S\theta C\phi S\eta \\ -C\phi S\eta - S\theta S\phi C\eta & C\theta C\eta & S\phi S\eta - S\theta C\phi C\eta \\ C\theta S\phi & S\theta & C\theta C\phi \end{bmatrix} \qquad (5)$$

where $\phi$, $\theta$, and $\eta$ are the tilting and rotation of the detector as shown in FIG. 5.

An x-ray projection of the object onto the detector plane (X, Y) can be calculated using the trigonometric relations as follows:

$$X = X_s^l - Z_s^l(X_s^l - X^l)/(Z_s^l - Z^l) \qquad (6a)$$

$$Y = Y_s^l - Z_s^l(Y_s^l - Y^l)/(Z_s^l - Z^l) \qquad (6b)$$

where $P_s^l = [X_s^l, Y_s^l, Z_s^l]^T$ and $P^l = [X^l, Y^l, Z^l]^T$ are the position vector of the x-ray source and the position vector of the object in the real detector coordinate system (l), respectively. Finally, the digitization of the image can be modeled as follows:

$$U = -S_f X + U_{offset} \qquad (7a)$$

$$V = -S_f Y + V_{offset} \qquad (7b)$$

where $S_f$ is the scale factor [pixel/mm] calculated by the scale module 48, and $U_{offset}$ and $V_{offset}$ are U and V distances separating the detector pixel of the origin of U and V from the piercing point, respectively. It is worth noting that the directions of the vectors U and V are opposite to the vectors X and Y, respectively. The scale factor can be taken from the manufacturer's specification or determined experimentally. Eleven parameters are used to characterize the cone-beam CT geometry: source position $(X_s, Y_s, Z_s)^l$, detector position $(Y_d, Z_d)^i$, detector tilt ($\phi$, $\theta$), detector rotation ($\eta$), piercing point ($U_{offset}$, $V_{offset}$), and gantry angle, t. These can be reduced to 9 independent variables by recognizing that (1) the origin of the detector coordinate system is on the line which connects the source and piercing point; therefore, the detector position can be expressed as one independent variable, and (2) the gantry angle is also determined by the source position, bringing the number of independent parameters to a total of nine.

The phantom 32 is placed approximately near the nominal iso-center of the instrument and the longitudinal direction of the phantom 32 is aligned roughly to the axis of rotation of the instrument. This guarantees that the phantom is visible in all projections. Since all measurements are referenced to the phantom, it is not necessary to place the phantom with great accuracy in the world coordinate system.

As described below, it is useful to eliminate the effect of the phantom location in space through determination of an alternative reference frame. For example, in the case of a gantry-based system, the determination of a reference frame that minimizes the discrepancy with respect to a simple circular trajectory permits the results of the calibration to be reported independent of the placement of the phantom (i.e. referenced to the mean circular motion that is expected from the gantry-based system).

As described above, the projection module 42 obtains first ellipse parameters $a_1, b_1, c_1, u_{01}, v_{01}$ that describe the first ellipse, which is the image projection of the first circle 34, and second ellipse parameters $a_2, b_2, c_2, u_{02}, v_{02}$ that describe the second ellipse, which is the image projection of the second circle 36, according to $$a(u-u_0)^2 + b(v-v_0)^2 + 2c(u-u_0)(v-v_0) = 1 \qquad (8)$$

where $(u_o, v_o)$ is the center of the ellipse. Once ellipse parameters are found, the detector angle, $\phi$, can be calculated using the following equations:

$$\sin\phi = -c_1\zeta_1/(2a_1) - c_2\zeta_2/(2a_2) \qquad (9)$$

$$\zeta_k = Z_s^I a_k/\sqrt{a_k}\sqrt{a_k b_k + a_k^2 b_k (Z_s^I)^2 - c_k^2}, \; k=1,2 \qquad (10)$$

where $\zeta$ is the intermediate parameter used in ellipse parameter calculation and subscript, k, indicates one of two circular group of ball bearings.

Also described above was the concept of the converging point: if the line $L_i$ is defined by $$L_i = I \cap D_i, \qquad (11)$$

were $D_i$ is i-th divergent plane and I is the detector plane (see FIG. 4), then the converging point is given by $$P_c = I \cap (D_1 \cap D_2 \cap \ldots) \qquad (12)$$
$$= I \cap L_d \qquad (13)$$

where, if all the lines connecting a pair of point objects are parallel, the intersection of divergent planes, $(D_1 \cap D_2 \cap \ldots)$, forms the one line, $L_d$. The concept of the piercing point is now used to first obtain the detector rotation angle $\eta$.

Calculation of Detector Rotation, $\eta$:

The rotation of the detector with respect to its normal axis is referred to as $\eta$. By identifying common features in the 3D circular pattern of BBs, and the projected elliptical pattern, it is possible to determine a value for $\eta$. The shape of the fitted ellipse on the virtual detector plane ($X^i$-$Y^i$) depends on the source position with respect to the phantom as shown in FIG. 5. By choosing two points at the extreme $X^i$ dimension on each of the two fitted ellipses, two pairs of points forming two lines parallel to $X^i$ are identified.

The location of these two points can be found from the numerical model of the ellipse. If the center of ellipse is assumed to be (0,0), then $$aU^2 + bV^2 + 2cUV = 1$$

or $$V^2 + \left(2\frac{c}{b}U\right)V + \left(\frac{a}{b}U^2 - \frac{1}{b}\right) = 0$$

When the discriminant of V equals to zero, the corresponding U equals either maximum or minimum value as follows:

$$\left(\frac{c}{b}U\right)^2 - \left(\frac{a}{b}U^2 - \frac{1}{b}\right) = 0$$

or $$U = \pm\sqrt{\frac{b}{ab-c^2}}$$

and $$V = -\frac{c}{b}U$$

Figure 7:
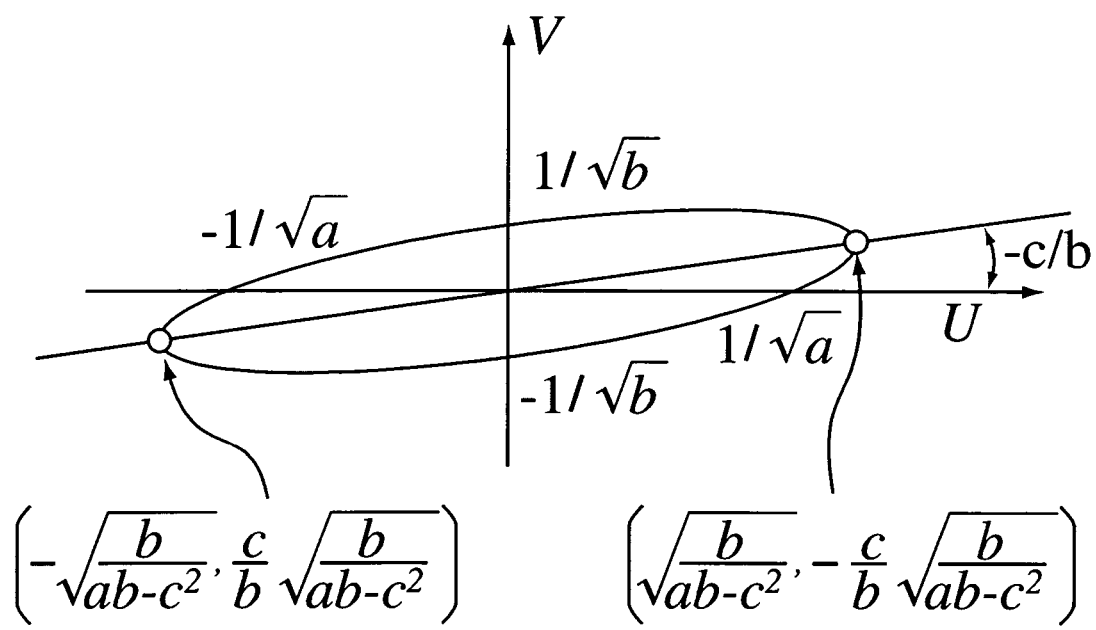
FIGS. 7 and 8 show geometric constructions used for obtaining coordinate data according to the principles of the present invention.

Since U has two real roots, and b is real positive, $ab-c^2$ is greater than zero. As shown in FIG. 7, the slope of the line passing through the two points found in the equations for U and V is determined by ellipse parameters. Two lines from each ellipse are used by the converging point module 50 to find the converging point, $P_\phi$.

Figure 8:
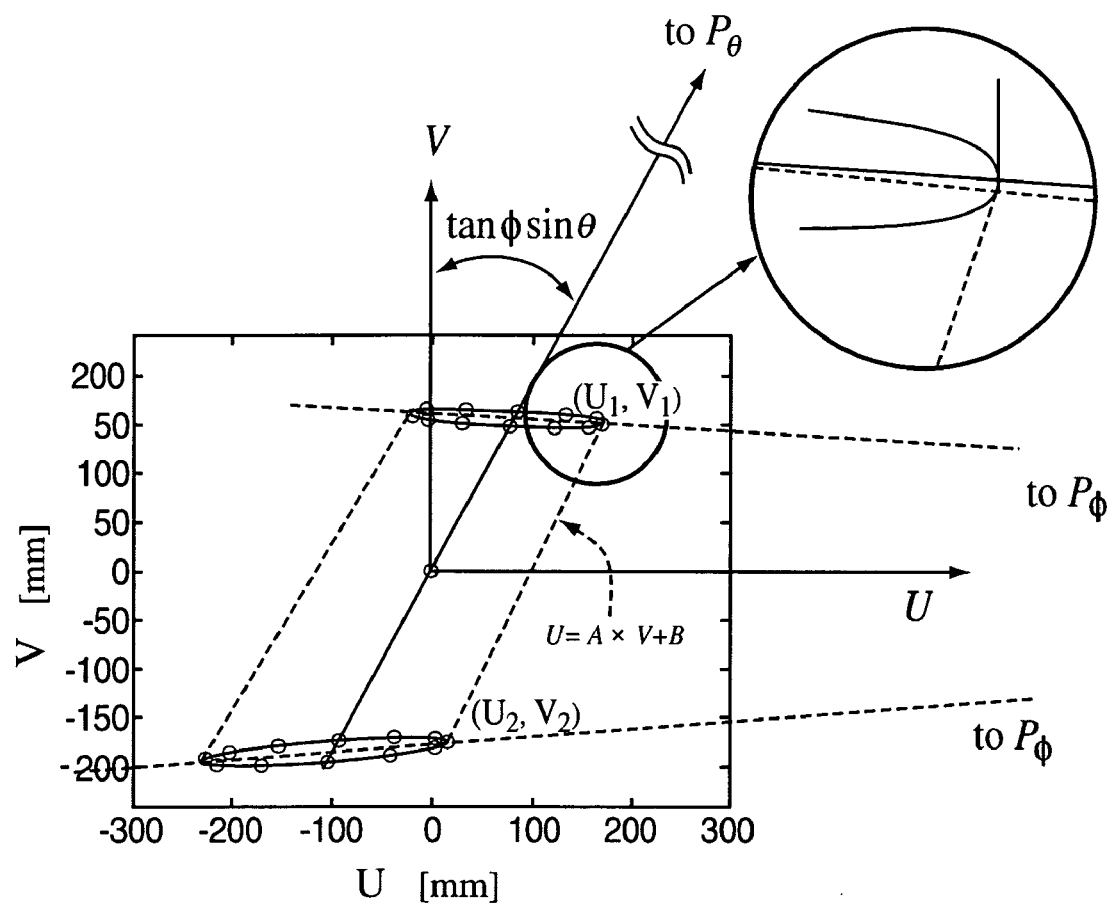

The last expressions for U and V may be generalized for very large detector angle, $\phi$ and $\theta$. (The converging point $P_\theta$ has an angle of $\tan\phi \times \sin\theta$ with the axis of V.) A line, which connects the outmost position of the two ellipses shown as dashed line in FIG. 8, may be used instead of using a parallel line to V-axis. The equation of the line can be written using two parameters, A and B as follows.

$$U = A \times V + B$$

The slope of the line, A, can be approximated using two points from each ellipse:

$$A \approx (U_1 - U_2)/(V_1 - V_2) = (U_1 - U_2)/(U_1 c_1/b_1 - U_2 c_2/b_2)$$

The condition of zero descriminant of each ellipse (k=1, 2) can be found as follows.

$$(c_k^2 - a_k b_k)B_k^2 + (a_k a^2 + b_k + 2c_k A) = 0$$

or $$B_k = \pm\sqrt{\frac{b_k + a_k A^2 + 2c_k A}{a_k b_k - c_k^2}}$$

where B has one trivial solution and it can be found easily by comparing the sign with $(U_1 + U_2)/2$. The generalizations of U and V are therefore $$V_k = -\frac{a_k A_k B_k + c_k B_k}{a_k A_k^2 + b_k + 2c_k A_k}$$

$$U_k = -A_k \frac{a_k A_k B_k + c_k B_k}{a_k A_k^2 + b_k + 2c_k A_k} + B_k$$

The previous expressions for U and V are recovered from these last two equations when A is zero.

Figure 9:
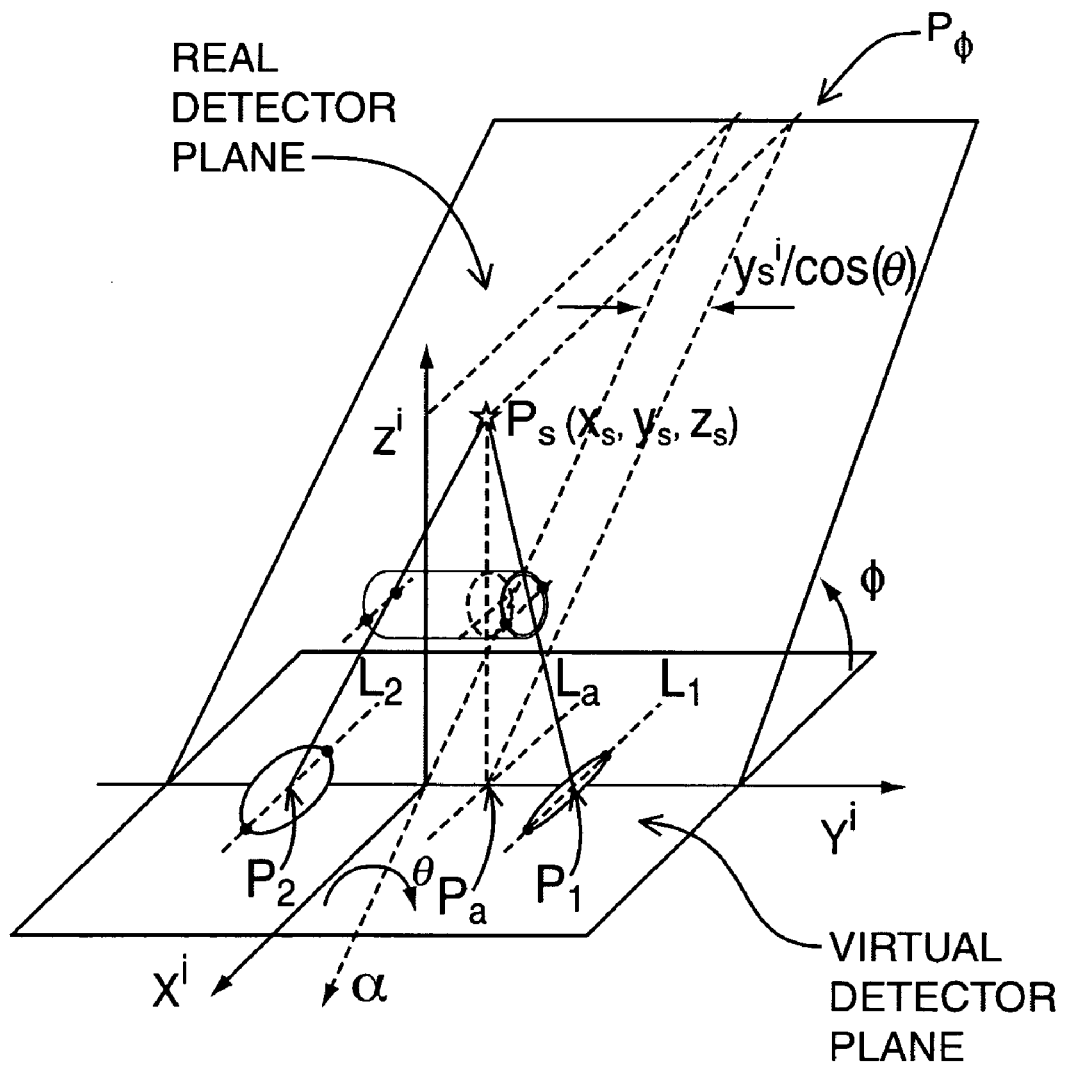
FIG. 9 shows the geometry of the virtual and real detector planes to obtain coordinate data according to principles of the present invention.

Referring to FIG. 9, lines connecting two pairs of points on the virtual detector plane ($X^i$ and $Y^i$) are denoted by $L_1$ and $L_2$. When the detector is tilted by $\phi$ around the axis of $Y^i$, these two lines converge to one point. The point is the converging point, $P_\phi$, due to the detector angle, $\phi$, and is the intersection of the axis of the divergent plane, and the real detector plane ($\alpha$ and $Y^i$) as explained below. If there are BBs in the phantom, shown as a broken circle in FIG. 9, the projected image of the BBs forms a line passing through point, $P_a$, on the virtual detector plane (i.e., the special case of an ellipse for which the length of the short axis is zero). The line, $L_a$, passes through the point, $P_\phi$, and is parallel to the axis $\alpha$. Since the ratio of short axis to long axis of the ellipse, $\sqrt{a_k/b_k}$ (k=1, 2), is proportional to the distance from the point, $P_a$, to the center of each ellipse, $P_1$ and $P_2$, the location of the point, $P_a$, can be found using the following equation, $$(P_0^a - P_0^2)/(P_0^1 - P_0^a) = \sqrt{a_2/b_2}/\sqrt{a_1/b_1}$$

or $$P_0^a = (P_0^1\sqrt{a_1/b_1} + P_0^2\sqrt{a_2/b_2})/(\sqrt{a_1/b_1} + \sqrt{a_2/b_2}) \qquad (14)$$

where $P_m^n$ is a position vector from point m to point n. The following is true as shown in FIG. 9.

$$P_0^a = Y_s^i/\cos(\theta) \quad (15)$$

Angles of lines, $L_1$ and $L_2$, with respect to line $L_a$ are proportional to the distance from the point, $P_a$, to the center of each ellipse, $P_1$ and $P_2$. The angle between the line, $L_a$ and $X^i$, or $\alpha$ and $X^i$ is the detector angle, $\eta$. When the detector rotation angle, $\eta$, is not zero, angles of lines in the real detector coordinate system are different by the detector rotation angle, $\eta$, as follows.

$$P_2^a/P_a^1 = A(\alpha,L_2)/A(\alpha,L_1) = (A(X^i,L_2)-\eta)/(A(X^i,L_1)-\eta)$$

or $$\eta = (P_a^1 A(X^i,L_1) + P_2^a A(X^i,L_2))/P_1^2 \quad (16)$$

where $A(p,q)$ is an angle between line p and line q. Once $\eta$ is known using the equation (16), the effect of $\eta$ can be corrected by rotating the image by $\eta$. Therefore, the remainder of the calibration procedure assumes that the detector rotation angle, $\eta$, has been estimated and corrected.

Figure 10:
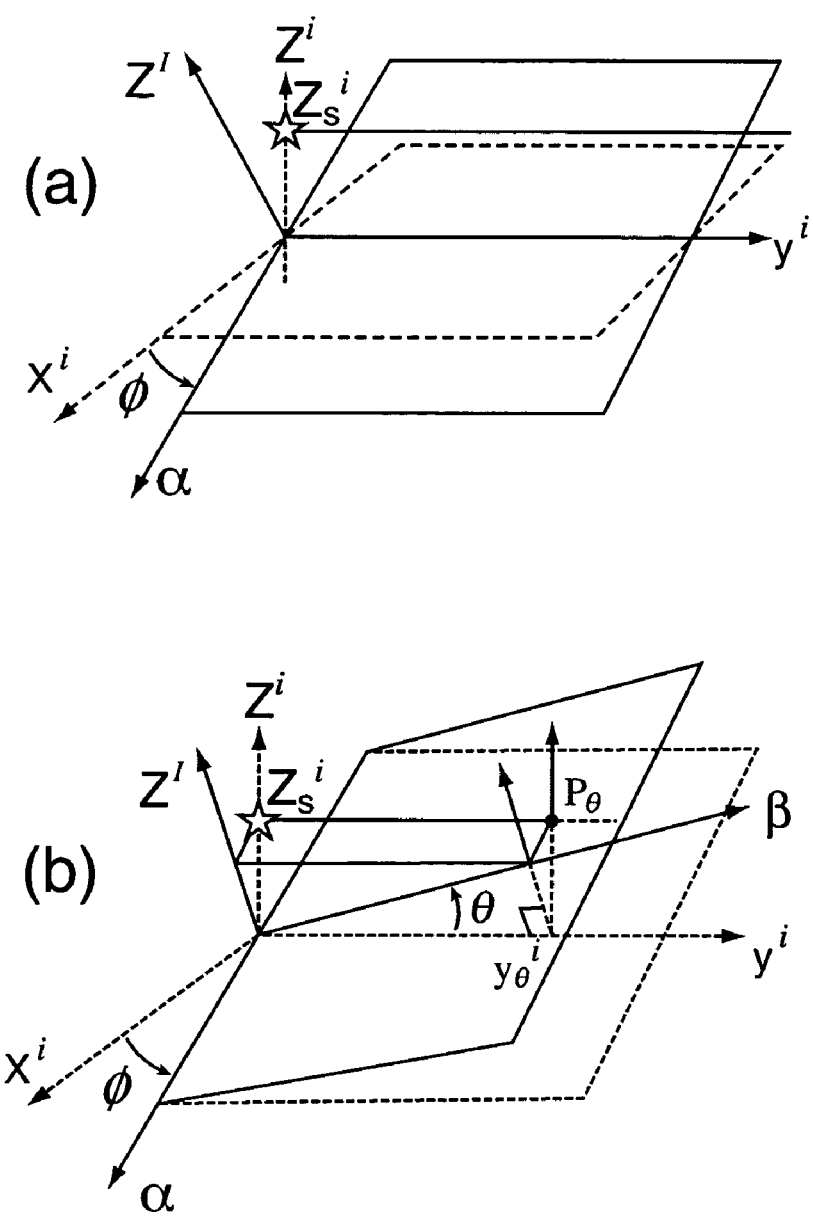
FIGS. 10A and 10B show a set of axes in relation to a converging point, as illustrated in FIG. 9, arising from detector tilt.

Calculation of Detector Tilt Angle, $\theta$ and $\phi$:

Using the pairs of ball bearings parallel to the $Z^w$ axis (FIG. 2D), the converging point, $P_\theta$, which is due to the detector angle $\theta$, can be found. The axis of divergent planes in this case is parallel to $Y^i$, which is parallel to $Z^w$, as shown in FIG. 10. The axis of divergent planes intersects the detector plane unless $\theta$ is zero (regardless to the angle of $\phi$). The converging point, $P_\theta$, has the following relationship as shown in FIG. 10.

$$\alpha_\theta = Y_\theta^i \tan(\theta)\tan(\phi)$$

$$\beta_\theta = Y_\theta^i/\cos(\theta) = Z_s^i \cos(\phi)/\sin(\theta) \quad (17)$$

and $$\tan(\phi)\sin(\theta) = \alpha_\theta/\beta_\theta \quad (18)$$

The location of the converging point, $P_\theta = (\alpha_\theta, \beta_\theta)$, can be found from the point of intersection of all the lines shown in FIG. 2C projected on the detector plane. Since the X-axis component of the source position in the virtual detector coordinate system is zero, $P_s^i = [0, Y_s^i, Z_s^i]$, the Z-axis component of the source position in the real detector coordinate system can be found as follows using equations (4) and (5).

$$Z_s^i = Z_s^i \cos(\theta)\cos(\phi) + Y_s^i \sin(\theta) \quad (19)$$
$$= \sin(\theta)\cos(\theta)(\beta_\theta + Y_s^i/\cos(\theta))$$

Figure 11:
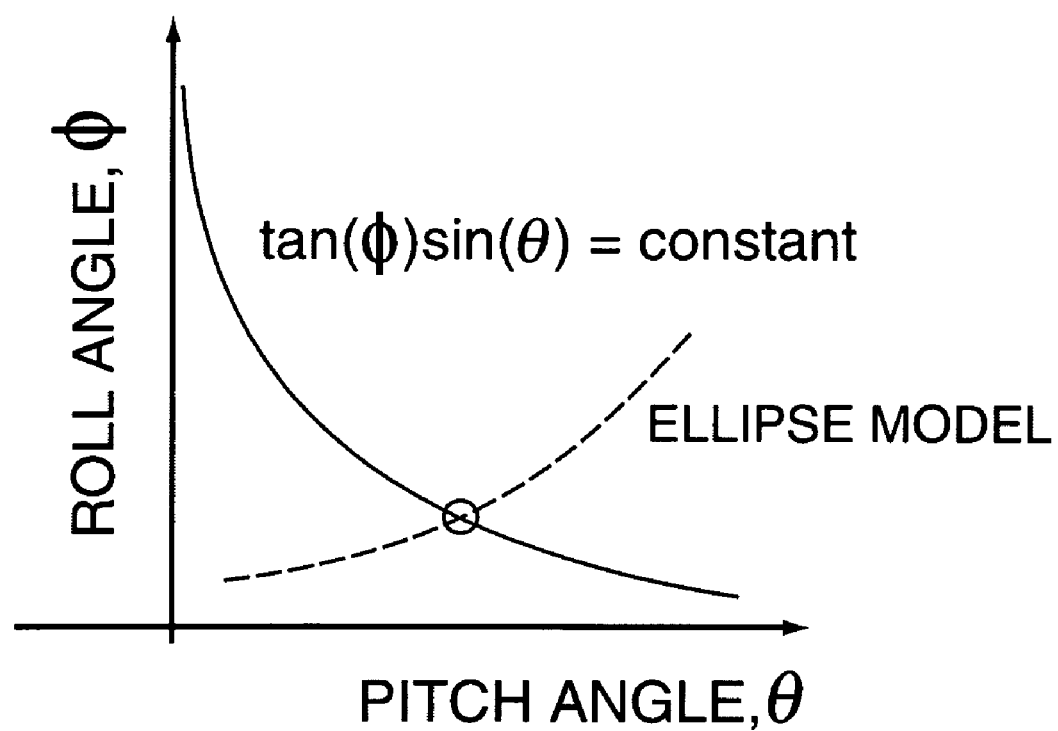
FIG. 11 shows a plot for obtaining a pitch angle and a roll angle of the detector of FIG. 1.

From the ellipse model in equations (9) and (10), $\phi$ is proportional to $Z_s^i$, when $ab-c^2$ is greater than zero (see FIG. 7). Since $\beta_\theta$ is known from the converging point of $P_\theta$ and $Y_s^i/\cos(\theta)$ is known from the converging point of $P_\phi$, $Z_s^i$ is simply a function of the detector angle of $\theta$, and is proportional to $\theta$ when is less than 45°. Therefore $\theta$ is proportional to $\phi$ in ellipse model as shown in FIG. 11. Intersection of two lines, one from equation (18) and the other from the equations (9), (10), and (19) is the solution of $\phi$ and $\theta$. This solution can be found using non-linear root finding method. There is a unique solution when the angle of $\theta$ is less than 45°, in accordance with equation (19).

Figure 12:
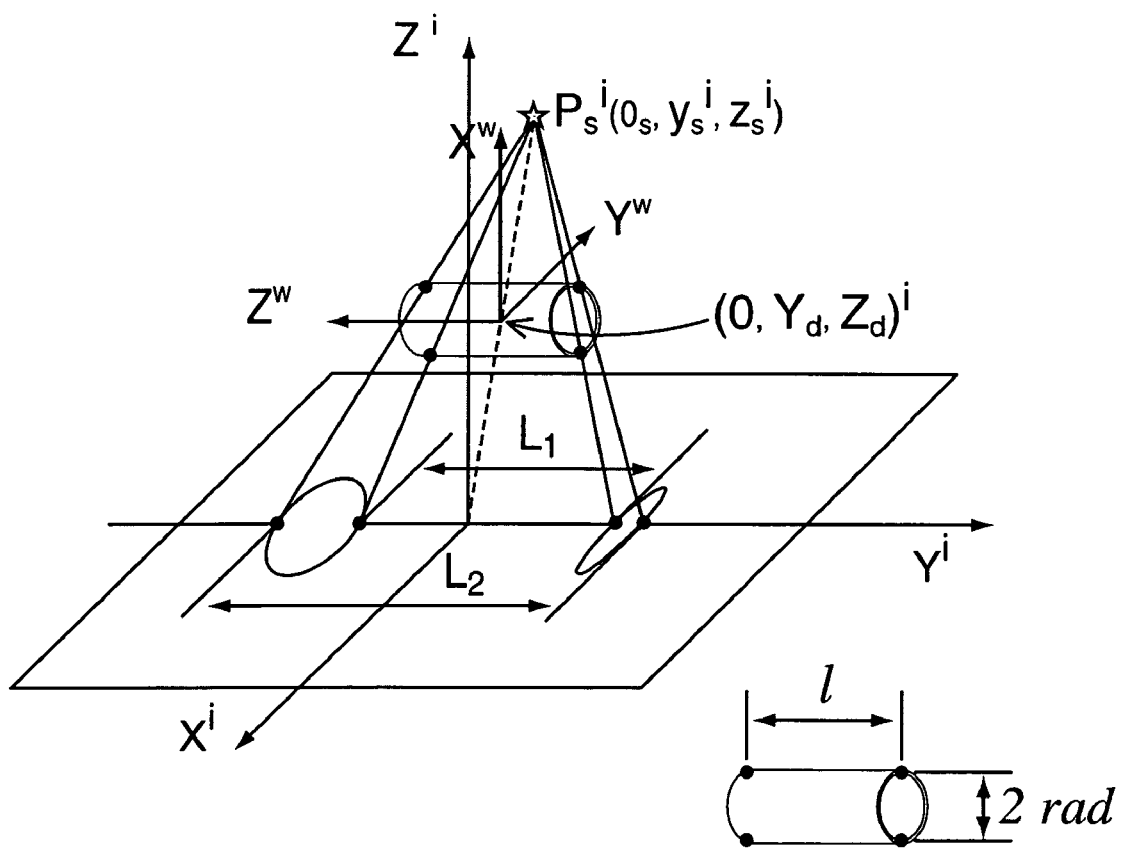
FIG. 12 illustrates a triangulation involving a source to detector distance according to the principles of the present invention.
Figure 13:
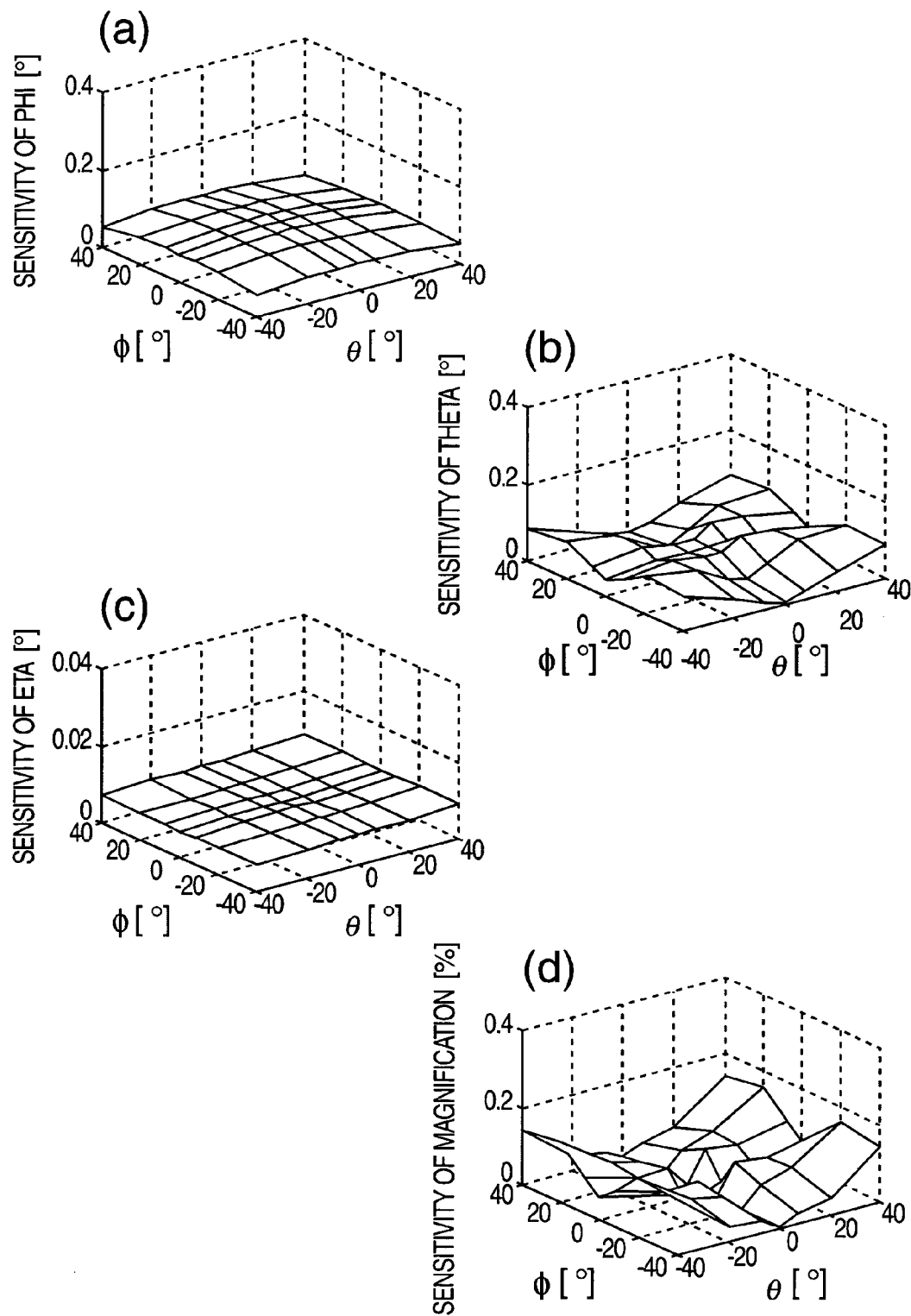
FIGS. 13A–D show plots of calibration sensitivity due to uncertainty of the position of the ball bearings shown in FIGS. 2A–E.

Calculation of Source Position $(X_s Y_s Z_s)^i$:

Once $\phi$ and $\theta$ are known, $Y_s^i$ and $Z_s^i$ can be found using equation (15) and (17), respectively. When $\theta$ is infinitesimally small (e.g. less than 0.001 degrees), however, equation (17) is not stable enough to estimate $Z_s^i$. When $\theta$ is this small, the following methods are used to estimate $Z_s^i$. The distance between two ellipses along the $Y^i$ axis, $L_1$ and $L_2$ have the following relations due to the triangulation as shown in FIG. 12.

$$L_1/Z_s^i = l/(Z_s^i - Z_d^i + rad) \quad (20)$$

$$L_2/Z_s^i = l/(Z_s^i - Z_d^i - rad) \quad (21)$$

where, rad and l are the radius of the circular pattern of ball bearing and distance between two circular trajectories, respectively. Combining two equations to calculate $Z_s^i$ gives, $$Z_s^i = (2\,rad\,L_1 L_2)/(l(L_2 - L_1)) \quad (22)$$

Knowing the three detector angles ($\eta$, $\phi$ and $\theta$) and the source position in the virtual detector coordinate system ($Y_s^i$ and $Z_s^i$), the source position in the real detector system can be calculated straightforwardly using equations (4) and (5) as follows. (Note: $X_s^i$ is zero by definition).

$$P_s^l = R_i^l P_s^i.$$

Calculation of Detector Position $(Y_d, Z_d)^i$:

One of the detector position vectors, $Z_d^i$, can be found from equations (20) and (21).

$$Z_d^i = Z_s^i(L_1 - l)/L_1 + r \quad (23)$$

Since the origin of the world coordinate system is on the line connecting the piercing point and the source, the following relationship is true.

$$Y_d^i = Y_s^i/Z_s^i Z_d^i \quad (24)$$

Gantry Angle Determination:

The nominal gantry angle, t, can be calculated by the following procedure. Equations (6.a) and (6.b) can be rewritten as follows.

$$(X_s^l - X)/(X_s^l - X^i) = (Y_s^l - Y)/(Y_s^l - Y^i) \quad (25)$$

or $$Y_s^l - Y^i = (X_s^l - X^i)(Y_s^l - Y)/(X_s^l - X) = p(X_s^l - X^i) \quad (26)$$

where $p = (Y_s^l - Y)/(X_s^l - X)$ can be calculated for each object point, $P^i = [X^i, Y^i, Z^i]^T$. Since all the other parameters except nominal gantry angle are known, $X^i$ and $Z^i$ are functions of nominal gantry angle, t, only. Rearranging equation (26) gives $$[b_1\ b_2][St\ Ct]^T = A \quad (27)$$

and $$b_1 = (pr_1 - r_4)x^w + (pr_3 - r_6)y^w$$

$$b_2 = (-pr_3 + r_6)x^w + (pr_1 - r_4)y^w$$

$$A = pX_s^i - Y_s^i - p(r_2(-z^w + Y_d^i) + r_3 Z_d^i) + r_5(-z^w + Y_d^i) + r_6 Z_d^i \quad (28)$$

where $x^w$, $y^w$ and $z^w$ are the position of the ball bearing in the world coordinate system, and elements of $R_i^l$ are denoted in the following way for convenience.

$$R_i^I = \begin{bmatrix} r_1 & r_2 & r_3 \\ r_4 & r_5 & r_6 \\ r_7 & r_8 & r_9 \end{bmatrix}$$

The nominal gantry angle can be found from equation (27) using the linear least squares method.

Experimental Testing and Validation:

The calibration algorithm was evaluated on the laboratory cone-beam CT system. Firstly, simple but accurate motions were applied to the x-ray source and detector by a computer controlled positioning system and their positions were compared to those calculated using the calibration method. In this test, the turntable, which holds the calibration phantom, was not rotated. Full rotation of the turntable was tested with angular increments of 1.2° and a fixed position of the x-ray source and detector. The calibration phantom was imaged at each angle and the calibration was estimated for every projection. Once all the calibration parameters were found with respect to the world coordinate system attached to the phantom, a search was performed and another coordinate system was identified which minimized the excursion of the x-ray source trajectory from a simple circle. All the calibration parameters were re-calculated with respect to this coordinate system. This approach permits inter-comparison of subtle changes in the calibration results independent of the placement of the phantom. Of course, applying this transformation obscures any gross changes in the geometry that can be described by a global rotation and/or translation.

The effect of precise geometric calibration on the quality in cone-beam CT reconstructions was examined. A thin steel wire (diameter of 0.16 mm) was positioned inside of the calibration phantom. CT compatible markers (two 3 mm plastic spheres and two 5 mm plastic spheres) were attached on the outside wall of the phantom 32. The calibration phantom 32 with wire and markers was imaged on the laboratory system (300 projections, 120 kVp, 1 mAs/projection, and 1.2°) with known perturbations of the system geometry during the collection of the projection data. The projection data was used for both the calibration and the CT reconstruction. The following perturbations were tested: (1) no disturbance, (2) 5 mm sinusoidal displacement of the x-ray source in y-z plane, (3) 5 mm sinusoidal displacement of the detector in y-z plane and (4) 5 mm sinusoidal displacement of the source and detector in x-y-z direction. The cone-beam CT reconstruction algorithm can accept the variation of source position, detector position, and detector tilt angle at every pose. However, only geometric features such as image scale, and detector tilt angle, are treated completely. The quality of the cone-beam CT images with and without perturbation correction was compared.

Accurate reconstruction requires accurate estimation of geometric parameters. The most critical geometric parameters on the cone-beam CT reconstruction are the piercing point (or the center of detector) and detector rotation angle $\eta$. The effect of piercing point on the cone-beam CT reconstruction and the correction with single BB were demonstrated. Small detector rotation ($\eta$) has subtle but visibly detrimental effects on the reconstruction image.

The accuracy of the calibration algorithm depends on the detector tilt, reducing as the detector tilt angles, $\phi$ and $\theta$, increase. The displacement of the phantom from the isocenter of the system did not significantly reduce the accuracy unless BBs appear overlapped in the projection image. The accuracy of piercing point estimation was not reduced due to the detector tilt angles. Since the detector tilt angles affect the calibration accuracy the most, the accuracy of the algorithm was analyzed as a function of the detector tilt angles, $\phi$ and $\theta$ in the geometry of a medical linear accelerator in which the source-to-detector distance (SDD) is 160 cm and the source-to-isocenter distance (SID) is 100 cm. The maximum error of the detector angles were found to be less than 0.05° for $\phi$ and $\theta$, and 0.005° for $\eta$ even at large detector angles ($\phi = \theta = \pm 40°$). In the practical range of the detector tilt angle, $\phi$ and $\theta << \pm 5°$, the error of the detector tilt angles, $\phi$, $\theta$, $\eta$, and magnification factor were negligible. The magnification factor was determined as the ratio of SDD to SID or $Z_s^i/(Z_s^i - Z_d^i)$. Error in the magnification factor was found to be less than 0.05% at a large detector tilt angle of $\pm 40°$. As discussed below, the inaccuracy of the algorithm is less than the uncertainties arising from the imperfections in phantom construction and BB detection. The sensitivity of the algorithm to these uncertainties should be taken into consideration.

The calibration method is an analytic method, which provides exact results when the positions of the BBs are exactly known and the number of BBs is larger than twelve. It is worth exploring the sensitivity of the calibration algorithm due to the uncertainty of the BB position. Although it is possible to derive direct analytic solutions for the sensitivity analysis, a numerical method is often preferred because of its simplicity. Thus, the resulting estimations in this study are approximate. The sensitivity, $\Delta X$, in an arbitrary calibration parameter, $X$, can be estimated in a root mean square sense as:

$$\Delta X = \delta \left( \sum_{i=1}^{} \left( \frac{\partial X}{\partial U_i} \right)^2 + \left( \frac{\partial X}{\partial V_i} \right)^2 \right)^{0.5} \quad (29)$$

where $\delta$ is the uncertainty of the ball bearing location, and $U_i$ and $V_i$ is the location of the i-th BB. The uncertainty of the ball bearing location may include manufacturing inaccuracies and uncertainty in the identification of the center $$\Delta X = \delta \left( \sum_{i=1}^{} \left( \left( \frac{X(U_i + dU_i) - X(U_i - dU_i)}{2 dU_i} \right)^2 + \left( \frac{X(V_i + dV_i) - X(V_i - dV_i)}{2 dV_i} \right)^2 \right) \right)^{0.5}$$

of a BB. Instead of calculating direct partial derivatives, the following equation was used to approximate the sensitivity of the calibration algorithm.

Table I summarizes the effect of number of ball bearings on the sensitivity for a system as exists on the medical linear accelerator (SDD=160 cm and SID=100 cm). The sensitivity analysis was based on the assumption that the uncertainty of ball bearing position was 0.1 pixels. This corresponds to the manufacturing inaccuracy of 25 μm or error of 0.1 pixels in the image processing. Since one ball bearing consists of more than 200 pixels in the image in this configuration, this is a reasonable assumption. Larger numbers of BBs reduced the uncertainty as shown in Table I. When the number of BBs was doubled from 16 to 32, the uncertainty of the source position, detector position, and detector angles were reduced by about 60%, 60% and 90% on average, respectively. Source and detector positions in the direction of beam, $Z_s^i$ and $Z_d^i$, were the most sensitive parameters to the uncertainty of ball bearing position. Although the uncertainty of $Z_s^i$ and $Z_d^i$, were about 0.12% (1.2 mm at SAD of 1000 mm for the phantom with 24 ball bearings), the uncertainty of the magnification factor, the ratio of SDD ($Z_s^i$) to SID ($Z_s^i - Z_d^i$), was relatively small (less than 0.01%). Therefore, the impact on the reconstructed image quality is expected to be negligible.

In the second test, the turntable was rotated for fixed positions of the x-ray source and detector. A total of 300 consecutive images were taken at increments of 1.2°. The piercing point was found as a function of turntable angle. The maximum movement of the piercing point during the turntable rotation was less than 0.1 pixels. The measured gantry (turntable) angle was compared with the encoder signal reported from the computer controlled positioning system. The maximum error of the turntable angle was about 0.05°. The uncertainty of the nominal gantry angle was about 0.01° and was smaller than the expected, 0.06°, as shown in Table I.

The measured trajectories of the x-ray source and detector are shown in FIG. 15A–D. Even though the angular precision of the turntable in the laboratory cone-beam CT was excellent, a small precession of about 0.0115° at three times per turntable revolution was observed. The wobbling or

TABLE I

Uncertainty in the calibration parameters for different numbers of ball bearings. Simulation condition is as follows: nominal gantry angle of zero degree, source to detector distance (SDD) of 1600 mm, source to axis of rotation distance (SAD) of 1000 mm, and detector tilting ($\phi$, $\theta$, $\eta$) of (0, 0, 0) degree. Uncertainty of ball bearing position is assumed to be 0.1 pixels.

| | source position | | detector position | | detector angle | | | | Magnification |
|---|---|---|---|---|---|---|---|---|---|
| N | $Y_s^i$ [mm] | $Z_s^i$ [mm] | $Y_d^i$ [mm] | $Z_d^i$ [mm] | $\phi$ [deg] | $\theta$ [deg] | $\eta$ [deg] | gantry angle, t [deg] | $Z_s^i/(Z_s^i - Z_d^i)$ [percent] |
| 12 | 0.29 | 1.89 | 0.14 | 1.15 | 0.09 | 0.089 | 0.0080 | 0.015 | 0.0093 |
| 16 | 0.17 | 1.50 | 0.10 | 0.92 | 0.11 | 0.077 | 0.0097 | 0.077 | 0.0081 |
| 20 | 0.15 | 1.34 | 0.09 | 0.82 | 0.09 | 0.069 | 0.0087 | 0.068 | 0.0072 |
| 24 | 0.14 | 1.23 | 0.08 | 0.75 | 0.09 | 0.063 | 0.0078 | 0.060 | 0.0066 |
| 32 | 0.12 | 1.06 | 0.07 | 0.65 | 0.07 | 0.054 | 0.0068 | 0.053 | 0.0057 |
| 40 | 0.11 | 0.95 | 0.07 | 0.58 | 0.07 | 0.049 | 0.0063 | 0.049 | 0.0051 |
| 60 | 0.09 | 0.78 | 0.05 | 0.47 | 0.06 | 0.040 | 0.0053 | 0.042 | 0.0042 |

FIGS. 13A–D show the sensitivity of the calibration parameters as a function of detector tilt angles, $\phi$ and $\theta$. The sensitivity of the algorithm appears a few times larger than the accuracy of the algorithm. The sensitivity of the algorithm, however, is very small even at very large detector tilt angles as shown in FIGS. 13A–D.

Figure 14:
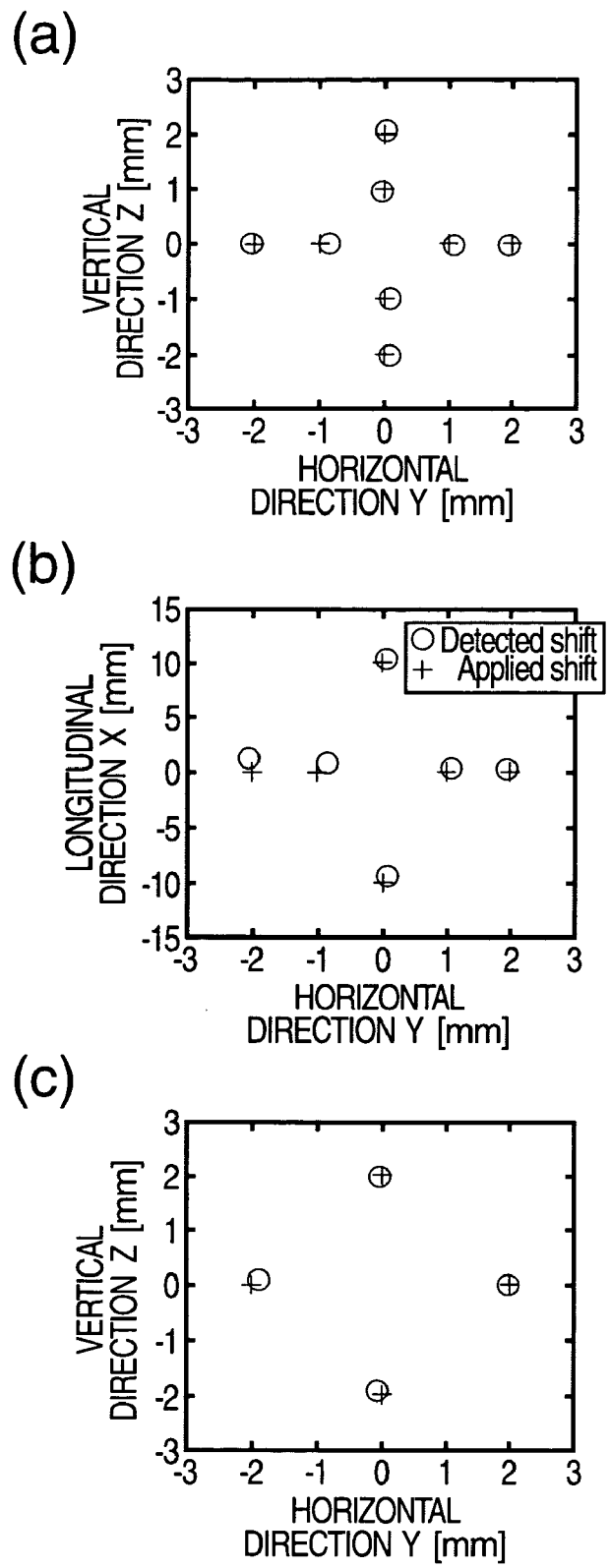
FIGS. 14A–C show plots testing calibration of the imaging instrument according to the principles of the present invention.
Figure 15:
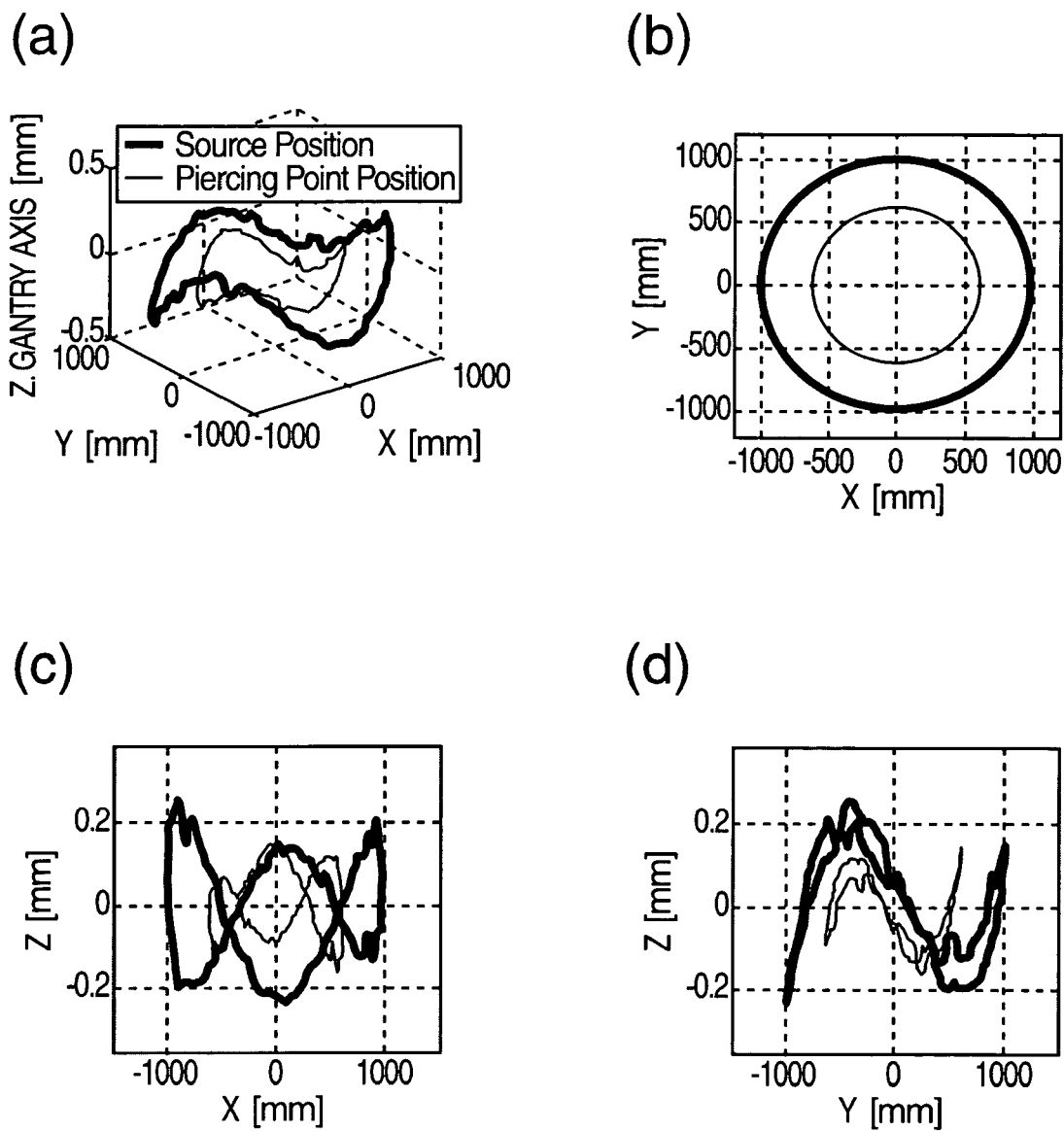
FIGS. 15A–D show plots of the source and piercing point positions according to the principles of the present invention.

The performance of the geometric calibration algorithm was evaluated on the laboratory system shown in FIG. 6A. A series of accurate displacements in source and detector position were applied and compared to those calculated using the calibration method. FIGS. 14A and 14B show the applied and measured results when the x-ray source is displaced. Applied movement by the computer-controlled positioning system is shown as a cross and location detected by the calibration algorithm is shown as a circle. Longitudinal, horizontal and vertical directions correspond to X, Y, and Z of the world coordinate system, respectively. Discrepancies in the x-ray source positions were found to be 0.08 mm in the direction normal to the beam (Y and Z axis direction) and 0.8 mm in the beam direction (X axis direction). These measured discrepancies are less than those determined through the sensitivity analysis (0.14 mm and 1.2 mm, respectively as shown in Table I), due to the conservative estimation of 0.1 pixel error employed in these calculations. Experimental results suggest that the effective pixel error would be about 0.06 to 0.07 pixels. FIG. 14C shows the calibration result when the detector position is moved—the discrepancy in the detector position was found to be about 0.06 mm.

precession of the turntable generates a "potato chip" shaped trajectory for the source and the center of detector in the rotating reference frame. The most important detector angle for the precise CT reconstruction, $\eta$, was found to be smaller than 0.01° for this system.

Figure 16:
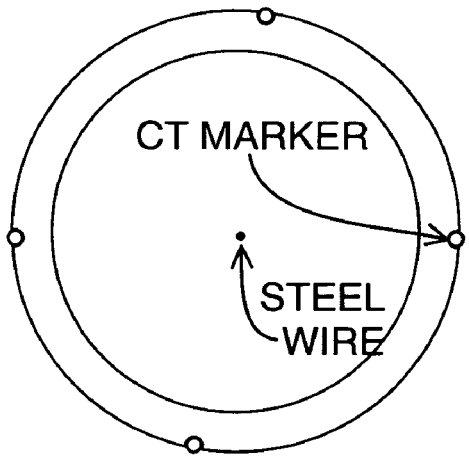
FIGS. 16A and 16B show axial slices of the cone-beam CT reconstruction of the steel wire in the calibration phantom of FIGS. 2A–E.
Figure 16:
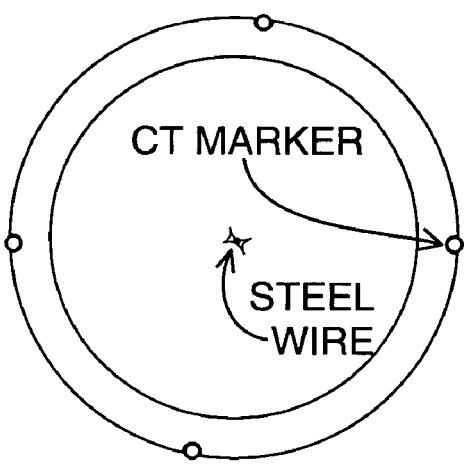
Figure 17:
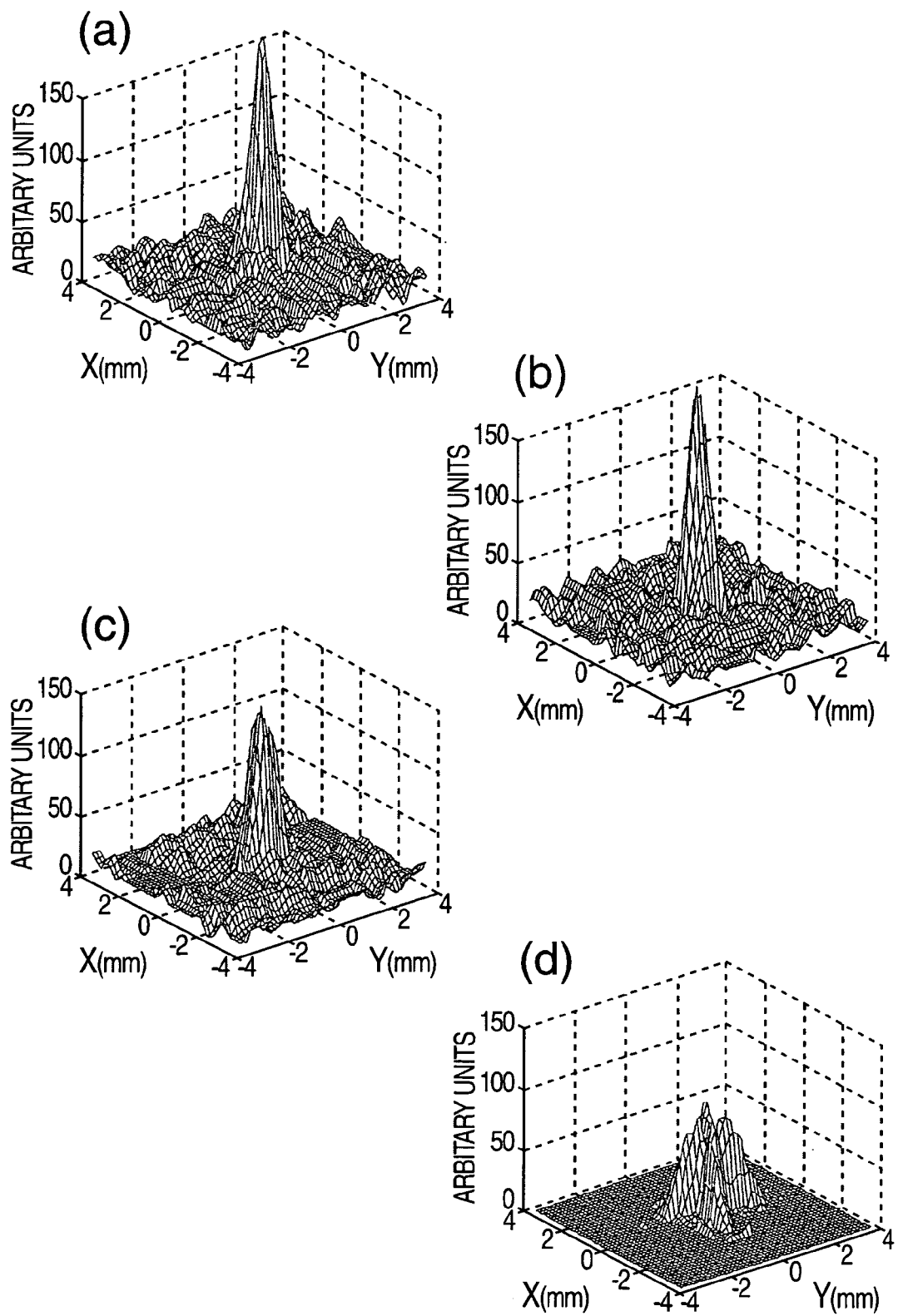
FIGS. 17A–D show surface plots of axial slice images of a thin steel wire in the calibration phantom of FIGS. 2A–E.

The effect of accurate geometric calibration on the quality of reconstructions was examined using a thin steel wire (diameter of 0.16 mm) positioned within the BB phantom at the time of calibration. As described above, four test conditions were explored: (1) circular motion with no disturbance, (2) 5 mm sinusoidal displacement of the x-ray source in y-z plane, (3) 5 mm sinusoidal displacement of the detector in y-z plane and (4) 5 mm sinusoidal displacement of the source and detector in x-y-z direction. These results were also compared to the image quality performance achieved using geometric parameters determined through careful mechanical alignment of the laboratory system (including iterative adjustment of the piercing point). FIGS. 16A–B show the cone-beam CT images using the calibration algorithm (a) and the mechanical calibration (b) for the most complex disturbance. The wire and plastic balls are shown clearly in FIG. 16A, but large distortion, artifact and blurring are found in FIG. 16B.

FIGS. 17A–D shows surface plots of the attenuation coefficients reported by the cone-beam CT method for a thin steel wire acquired with (a) the circular motion with the calibration method, (b) complex disturbance with the calibration, (c) circular motion without calibration, and, (d) complex disturbance without calibration. The intensity of the cone-beam CT image of a thin wire was symmetric and the full width at half maximum (FWHM) was 0.78 mm. Improvement in the peak signal was 53% in the steel wire on average across the four different cases as shown in Table II. The signal from the wire was consistent when the calibration method was used regardless of the disturbance applied. Artifact and distortion around the marker was also reduced. On average, improvement in FWHM of the steel wire was 28%.

TABLE II

Influence of calibration on the reconstruction of a steel wire. The dataset was acquired on the bench top CBCT system with mechanical determination of the imaging geometry assuming a circular trajectory.

|  | FWHM (mm) | Signal (arbitrary) |
| --- | --- | --- |
| Without calibration algorithm | 0.99 mm | 0.27 |
| With calibration algorithm | 0.78 mm | 0.41 |
| Improvement | 28% | 53% |

As described below in greater detail, similar tests were performed on a medical linear accelerator. In these investigations, an error in geometric scale was identified. The diameter of the phantom was 5% larger than manufacturing specifications and agreed within 0.2% when the full calibration method was employed. This large error in the dimensional accuracy in cone-beam CT on the medical linear accelerator was due to the use of a nominal SDD (160 cm vs 153 cm) in the previous calibration scheme.

Figure 18:
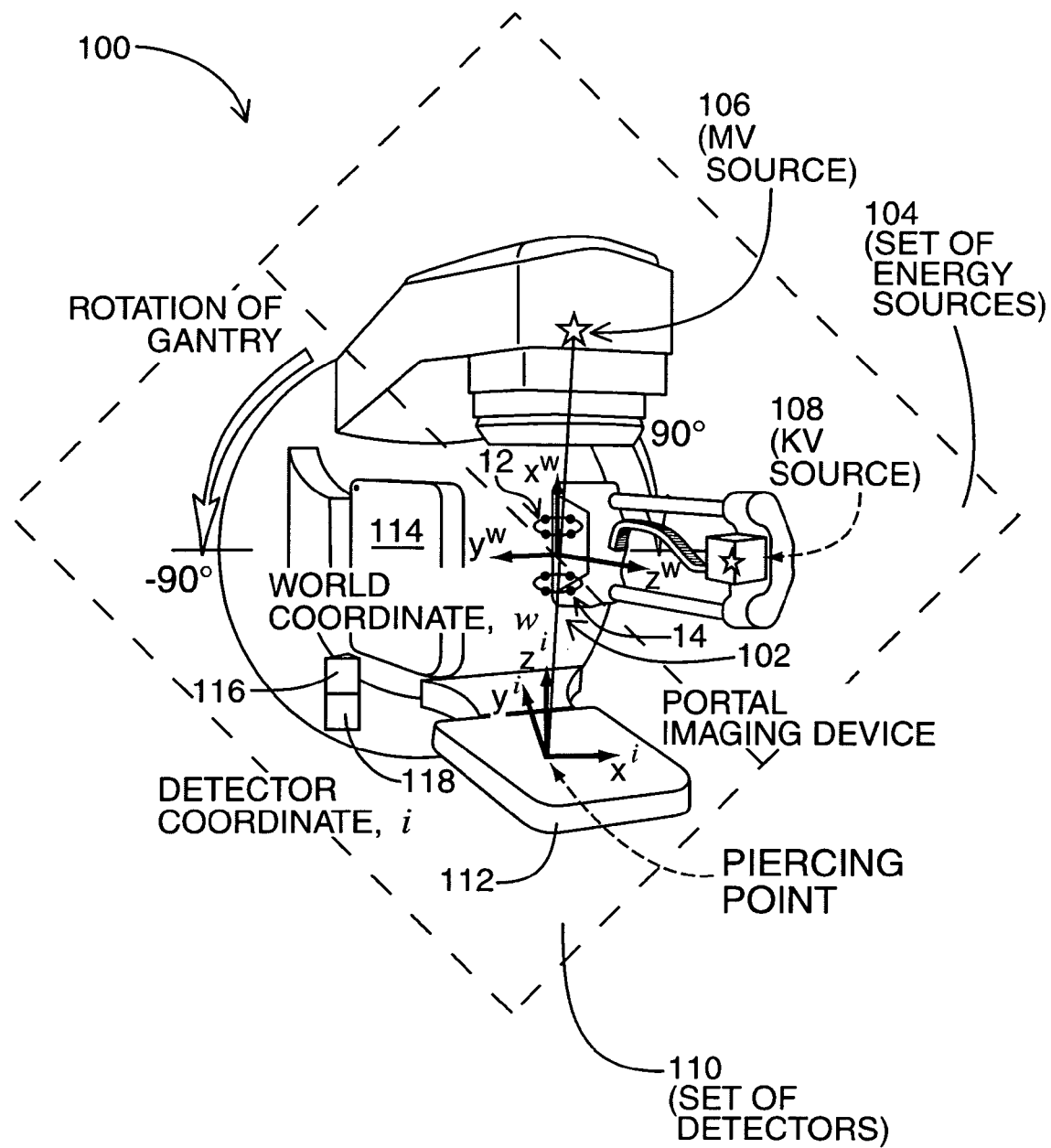
FIG. 18 shows a system for obtaining coordinate data of a source and detector instrument according to the principles of the present invention.

FIG. 18 shows a system 100 for obtaining coordinate data of a source and detector instrument. The system 100 includes a marker assembly 12 having a plurality of markers 14 with a particular geometry, the marker assembly 12 being disposed in a targeting region 102.

A set of energy sources 104 contains at least one member for bombarding the plurality of markers 14 with energy. In the embodiment shown, two such members 106 and 108 are provided. The energy source 106 is a MV x-ray source for targeting an object, an organism or part thereof. For example, the energy source 106 may be used for radiation therapy to treat a malignant tumor in a human. The other energy source 108 is a kV x-ray source used for imaging the organism to aid in the delivery of radiation from the energy source 106.

The system 100 also includes a set of detectors 110 containing at least one member, wherein energy emitted from any one member of the set of energy sources 104 may be detected by at least one member of the set of detectors 110. In the embodiment shown, the detector 112 detects energy emitted from the source 106, while the detector 114 detects energy from the source 108.

In another embodiment, there may be a plurality of sources, but only one detector that detects energy from all these sources. For example, in a triangular arrangement, two sources and one detector can be placed at the corners of a triangle. Conversely, in yet a different embodiment, there may be a plurality of detectors for detecting energy from a single source.

An image device 116 includes software and hardware coupled to the set of detectors 110 that processes information captured by the detectors to form image data of the plurality of markers 14. The image device 116 can consist of a central device to which information from the detectors is funneled. Alternatively, the device can consist of a plurality of devices, one for each detector, dispersed where each detector is disposed.

A calibration module 118 utilizes information about the particular geometry of the plurality of markers 14 and the image data to determine coordinate data of at least one of the set of energy sources 104 and the set of detectors 106.

The above-described analytical method for obtaining coordinate data may be applied to the system 100 to obtain location coordinates of the set of sources 104, and position/orientation coordinates of the set of detectors 110, which data may be used to cross-calibrate the imaging system, which includes the source 106 and detector 112, and the delivery system, which includes the source 108 and the detector 114.

In particular, the position/orientation of the imaging system source 106 and detector 112 may be obtained with respect to the world reference frame. Likewise, the position/orientation of the delivery system source 108 and detector 114 may be obtained with respect to the same world reference frame. More generally, the position/orientation of the imaging system source 106 and detector 112 may be obtained with respect to a plurality of reference frames, and the position/orientation of the delivery system source 108 and detector 114 may be obtained with respect to the same plurality of reference frames. Finding these coordinates with respect to a common reference frame(s) affords the opportunity to cross-calibrate the imaging system and the delivery system, where cross-calibrating two components involves relating coordinate data of one component to coordinate data of the other component.

It should be emphasized that the principles of the present invention can be used to cross-calibrate any of the components of a source and detector system comprising a plurality of sources and a plurality of detectors. The source and detector system might just comprise components for imaging, and be devoid of any components for therapeutic delivery of energy, and vice versa.

It should be noted that the geometry of the marker assembly 12 permits concurrently disposing a target (not shown), consisting of an object, an organism, or a part thereof, and the plurality of markers 14 within the targeting region 102. The target and the marker assembly 12 in the targeting region 102 may both be bombarded with energy packets simultaneously. This affords the opportunity to simultaneously image the object or organism and determine the pose of the source and detector system. For example, in a system with a non-rigid, irreproducible geometry, where a reproducible geometric calibration cannot be obtained, the invention could be used to simultaneously acquire one or multiple projections of the object or organism along with the source and detector pose for each projection.

The results of experiments applying some of the principles of the present invention to the system 100 of FIG. 18 are now provided. First, the sensitivity of the calibration algorithm on the inaccuracy of BB identification due to limitations of image quality or limited accuracy of the phantom dimension is analyzed. Table III shows the uncertainty of the calibration parameter due to 0.5 pixel error. The pixel error of the BB position in kV image is less than 0.1 pixels for the marker assembly 12 for system 100. However, the poor quality of the portal image compared to the kV diagnostic image gives poorer estimation, and pixel error seems to be about 0.5 pixels on average. Larger ball bearings and higher monitor units (MU) can be used to make better portal images of the phantom.

TABLE III

Uncertainty in geometric parameters for different number of ball bearings and 0.5 pixel error in BB localization.

| N | source position $Y_s^i$ [mm] | $Z_s^i$ [mm] | detector position $Y_d^i$ [mm] | $Z_d^i$ [mm] | detector angle $\phi$ [deg] | $\theta$ [deg] | $\eta$ [deg] | gantry angle, t [deg] | Magnification $Z_s^i/(Z_s^i - Z_d^i)$ [percent] |
|---|---|---|---|---|---|---|---|---|---|
| 12 | 1.1925 | 9.4450 | 0.7180 | 5.7435 | 0.4515 | 0.4430 | 0.0400 | 0.0760 | 0.0465 |
| 16 | 0.8545 | 7.5175 | 0.5155 | 4.5890 | 0.5420 | 0.3840 | 0.0485 | 0.3840 | 0.0405 |
| 20 | 0.7620 | 6.7150 | 0.4595 | 4.0990 | 0.4660 | 0.3435 | 0.0435 | 0.3385 | 0.0360 |
| 24 | 0.6955 | 6.1295 | 0.4195 | 3.7420 | 0.4425 | 0.3135 | 0.0390 | 0.3020 | 0.0330 |
| 32 | 0.6025 | 5.3085 | 0.3635 | 3.2405 | 0.3730 | 0.2715 | 0.0340 | 0.2660 | 0.0285 |
| 40 | 0.5385 | 4.7480 | 0.3250 | 2.8985 | 0.3370 | 0.2430 | 0.0315 | 0.2465 | 0.0255 |
| 60 | 0.4400 | 3.8770 | 0.2655 | 2.3665 | 0.3015 | 0.1980 | 0.0265 | 0.2110 | 0.0210 |

Figure 19:
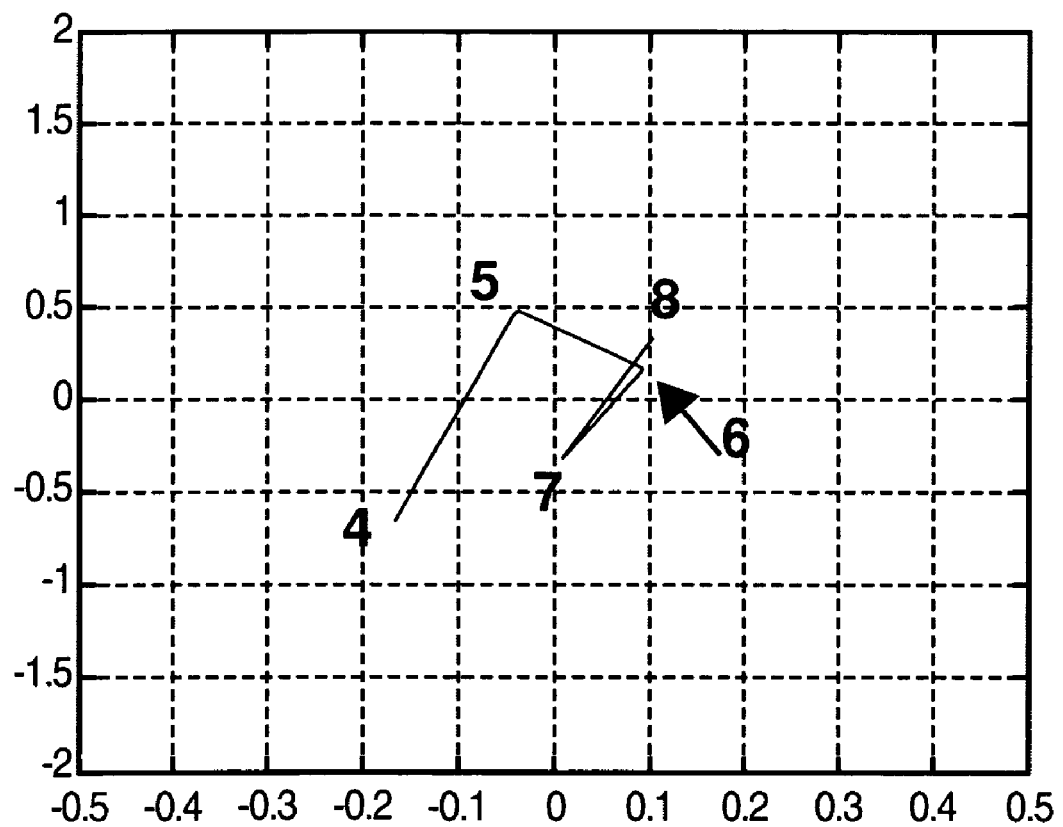
FIG. 19 shows the trajectory of electrons on a target in the system shown in FIG. 18.

Megavoltage beam stability is tested first. At fixed gantry angle of the source 108, nine images of phantom are taken continuously. The position of the electron beam on the target was found to vary over the first nine images. FIG. 19 shows the trajectory of the electrons on the target, where the Z-axis is the direction pointing out from iso-center away from gantry. Since the first couple of images and the last image are extremely poor, those images could not be used. The beam position is controlled very well in the direction of cross plane (Y axis). Range of motion in Y and Z direction is about 0.3 mm and 1.5 mm, respectively.

Figure 20:
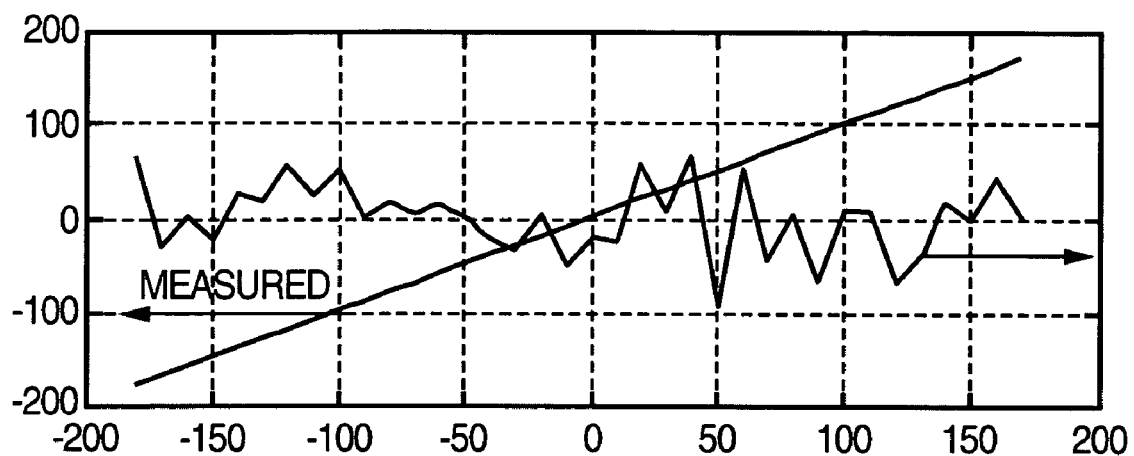
FIG. 20 shows the nominal gantry angle from the linear accelerator console and measured gantry angle from the calibration in the system shown in FIG. 18.

The nominal gantry angle and measured gantry were compared. Thirty-six portal images were taken at gantry angles spaced at 10 degrees. Ten MU are given at each gantry angle. Geometric parameters such as source position, detector position and tilt angle, and gantry angle were calculated at each angle. FIG. 20 shows the nominal gantry angle reported by the linear accelerator console and measured gantry angle from the calibration. Maximum error of the gantry angle is always less than 0.1 degree as shown in FIG. 20.

Figure 21:
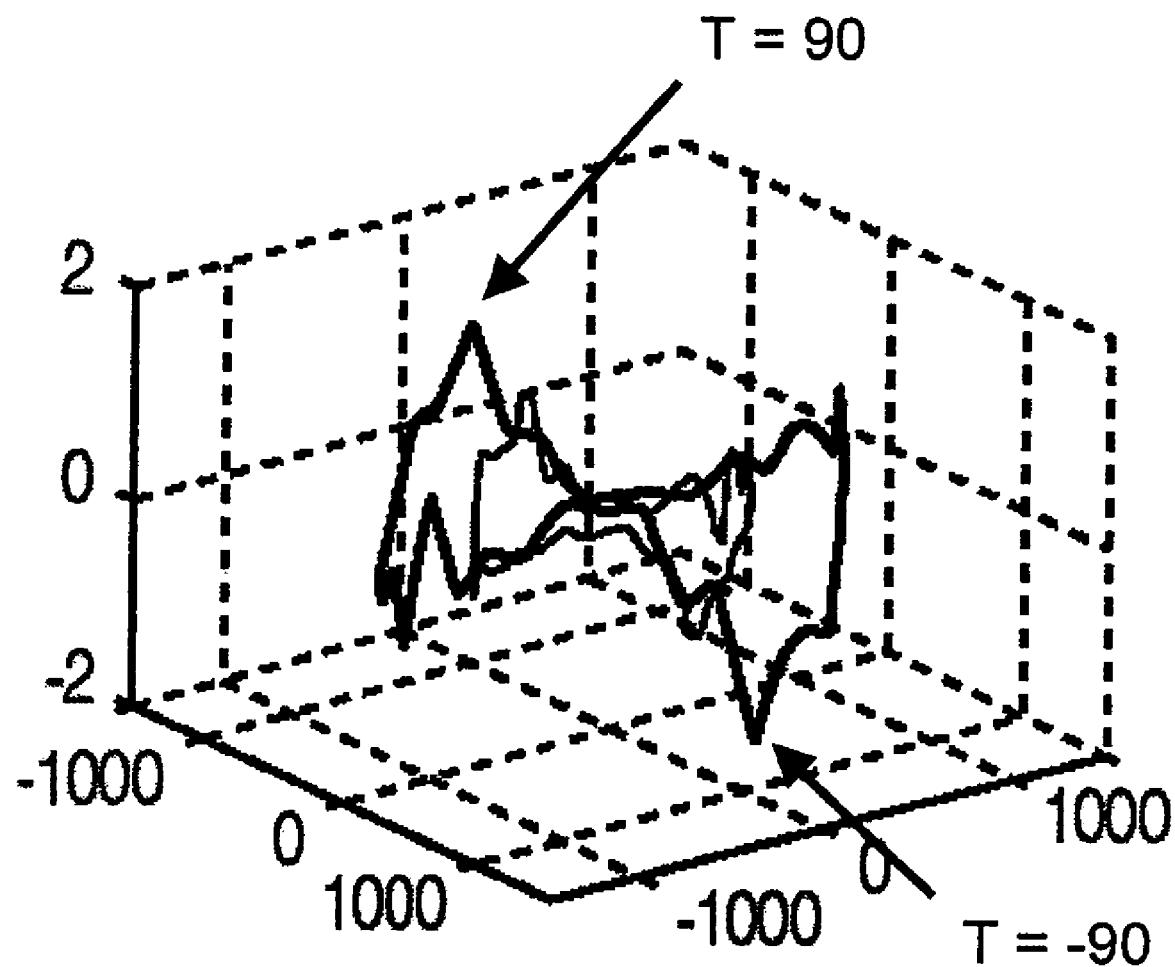
FIG. 21 shows the MV source position and piercing point on the detector in three-dimensional spaces in the system shown in FIG. 18.

FIG. 21 shows the MV source position and piercing point on the detector in 3 dimensional spaces. Average source to iso-center distance (SAD) is 1003.2 mm and source to detector distance is 1600.4 mm. The maximum deviation of the beam position from the ideal trajectory of a perfect circle is found at gantry angles of –90 degree and 90 degree. The MV source moves toward the gantry by 1.2 mm and toward the couch by 1.2 mm again at gantry angle of –90 and 90 degree, respectively. This movement is also found from the analysis of piercing point movement as a function of gantry angle.

Figure 22:
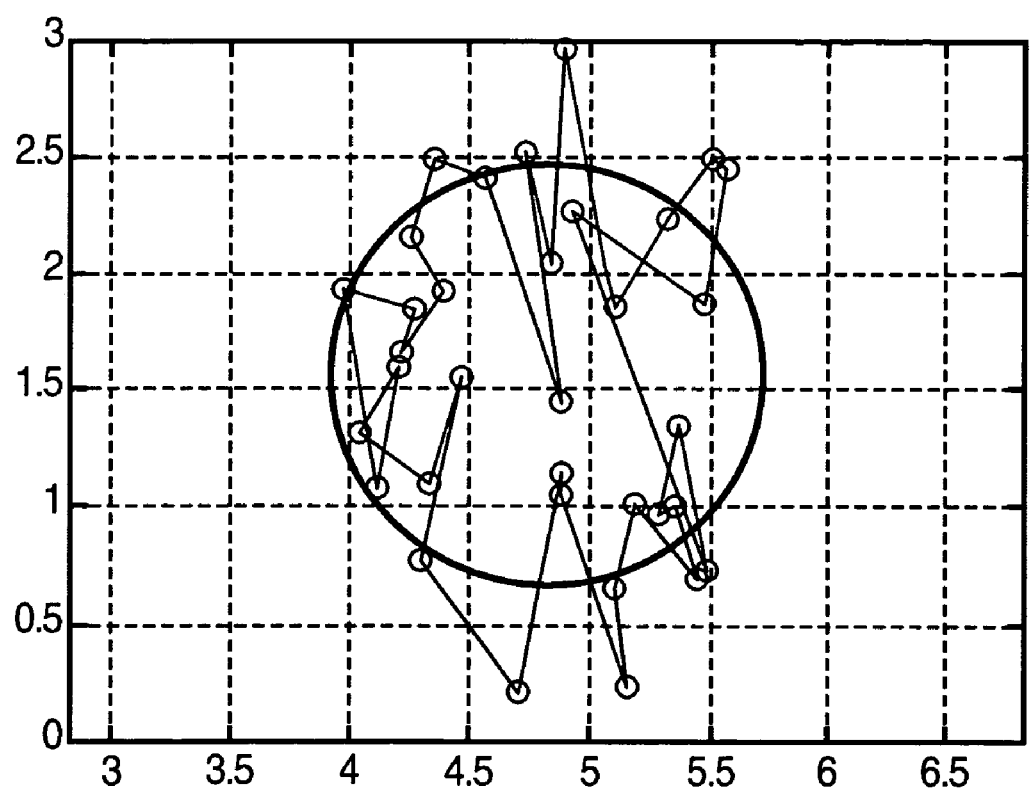
FIG. 22 shows the alignment of collimator rotational axis to the MV source position in the system shown in FIG. 18.

FIG. 22 shows the alignment of collimator rotational axis to the MV source position. The collimator rotational axis can be found by attaching the phantom to the collimator. Thirty-six images are taken by rotating collimator with the phantom. Ten MU is given to each image. The source position in the rotating coordinate system fixed in the phantom will stay at a point when the source is at the axis of collimator rotation. If the source is at distance from the axis of collimator rotation, the source position follows a circular trajectory around the axis of collimator rotation. Thin lines with small circles represent the raw data of source positions in rotating coordinate system of the phantom. The axis of rotation can be found by averaging the source position. The average distance of the source positions from the center indicates the distance between source position and the axis of collimator rotation. Thick lines represent the average motion of the source around collimator axis. It was found to be 0.9 mm.

Figure 23:
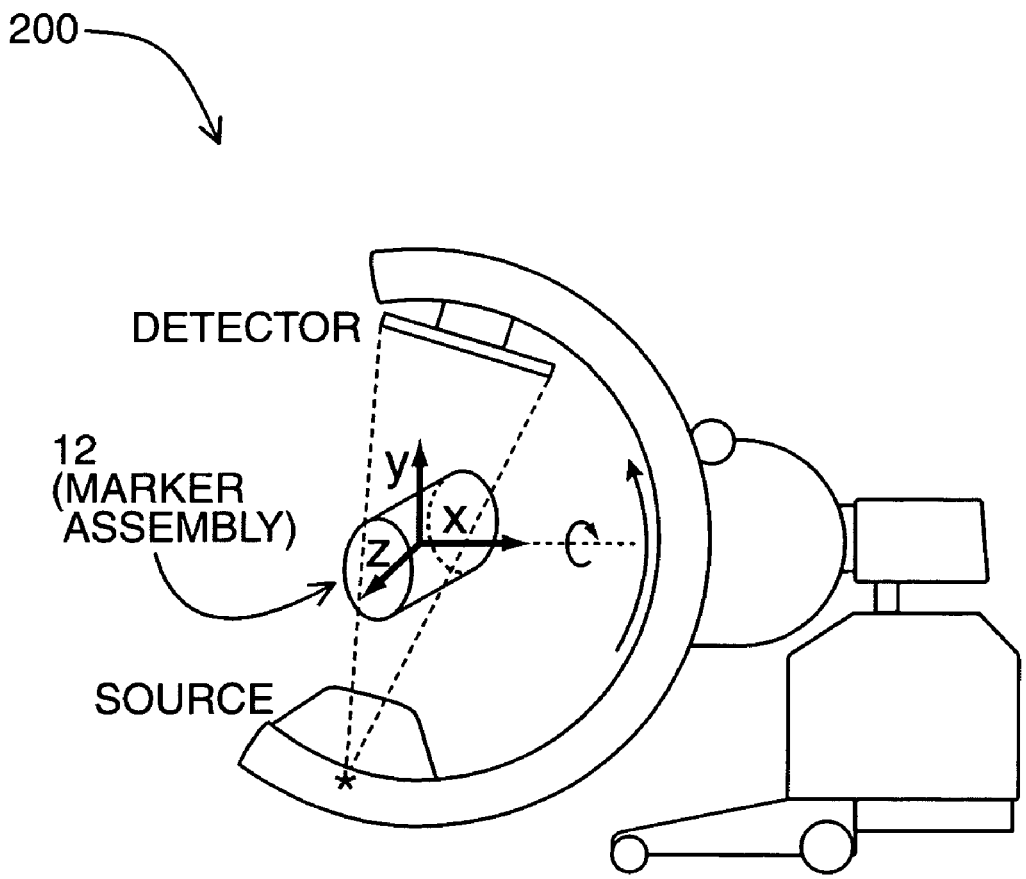
FIG. 23 shows a fluoroscopic C-arm instrument and a marker assembly according to the principles of the present invention.

It should be understood that various modifications and adaptations could be made to the embodiments described and illustrated herein, without departing from the present invention. For example, many types of imaging devices can benefit from the principles of the present invention. FIG. 23, for instance, shows a C-arm instrument 200 used for fluoroscopy in interventional radiology. A marker assembly 14 is also shown. By imaging the marker assembly 14 and performing the analysis described above, the instrument 200 can be calibrated according to the principles of the present invention.

It should be further understood that the method for calibration can be repeated at as many nominal gantry angles as desired. At each gantry angle, the geometry of the marker assembly 12 and the image data obtained at that gantry angle yield the nine parameters $(X_s, Y_s, Z_s)$, $(X_d, Y_d, Z_d)$ and, $(\theta, \phi, \eta)$. Obtaining coordinate information at several gantry angles affords the opportunity to study motion of the source as a function of time (e.g., MV focal spot motion). Thus, a series of subsequent poses and a time-based detector system can be used to track motion, calibrating the coordinate data obtained at each pose according to the principles of the present invention.

The scope of the invention is to be defined in the appended claims.

What is claimed is:

1. A system for obtaining coordinate data of a source and detector instrument, the system comprising:
   a marker assembly having a plurality of markers with a particular three dimensional geometry, wherein the plurality of markers describe a first circle and a second circle that are parallel and lie on a cylinder;
   an energy source for targeting the plurality of markers with energy packets;
   a detector for detecting energy packets after the plurality of markers have interacted therewith;
   an image device for forming image data of the plurality of markers from the energy packets detected by the detector, wherein the image data correspond to a first ellipse associated with a first projection of the first circle onto the detector and a second ellipse associated with a second projection of the second circle onto the detector;
   a calibration module including at least one equation, for non-iteratively determining, from the particular geometry of the plurality of markers and the image data, in a world coordinate system, coordinate data that includes a pitch of the detector, when coordinate data for the detector is obtained, wherein the calibration module comprises: a projection module for obtaining first ellipse parameters that describe the first ellipse and second ellipse parameters that describe the second ellipse; and a marker assembly module for obtaining geometric parameters of the marker assembly, the calibration module determining the coordinate data from the first ellipse parameters, the second ellipse parameters and the geometric parameters of the marker assembly;

wherein the calibration module further comprises:

an intersection module for determining a location of an intersection point where lines connecting points on the first ellipse to opposite points on the second ellipse intersect; and a scale module for obtaining a scale factor corresponding to the image data, wherein the calibration module determines the coordinate data from the first ellipse parameters, the second ellipse parameters, the geometric parameters of the marker assembly, the intersection point and the scale factor.

2. The system of claim 1, wherein the coordinate data is used to calibrate the source and detector instrument.

3. The system of claim 1, wherein the coordinate data includes three source coordinates defining a position of the energy source, three detector position coordinates defining a position of the detector and three detector orientation coordinates defining an orientation of the detector, one of the three detector orientation coordinates being an angle specifying the pitch of the detector, thereby to enable the pose of the source and detector instrument to be determined.

4. The system of claim 1, wherein the energy source includes at least one of an electromagnetic wave source, a particle accelerator and a radionuclide source.

5. The system of claim 1, wherein the energy source includes at least one of an x-ray source, a gamma ray source, an atomic source, a sub-atomic source, and an optical photon source.

6. The system of claim 1, wherein the source and detector instrument includes one of a radiography instrument, a stereography instrument, a bi-plane imaging instrument, a fluoroscopy instrument, a tomosynthesis instrument, and a tomography instrument.

7. The system of claim 1, wherein each of the markers is a metallic sphere.

8. A system for obtaining coordinate data of a source and detector instrument, the system comprising:

a marker assembly having a plurality of markers with a particular three dimensional geometry, wherein the plurality of markers describe a first circle and a second circle that are parallel and lie on a cylinder;

an energy source for targeting the plurality of markers with energy packets;

a detector for detecting energy packets after the plurality of markers have interacted therewith;

an image device for forming image data of the plurality of markers from the energy packets detected by the detector, the image data associated with a single view of the plurality of markers, wherein the image data correspond to a first ellipse associated with a first projection of the first circle onto the detector and a second ellipse associated with a second projection of the second circle onto the detector;

a calibration module including at least one equation, for non-iteratively determining, from the particular geometry of the plurality of markers and the image data, in a world coordinate system, coordinate data that includes a pitch of the detector, when coordinate data for the detector is obtained, wherein the calibration module comprises: a projection module for obtaining first ellipse parameters that describe the first ellipse and second ellipse parameters that describe the second ellipse; and a marker assembly module for obtaining geometric parameters of the marker assembly, the calibration module determining the coordinate data from the first ellipse parameters, the second ellipse parameters and the geometric parameters of the marker assembly;

wherein the calibration module further comprises:

an intersection module for determining a location of an intersection point where lines connecting points on the first ellipse to opposite points on the second ellipse intersect; and a scale module for obtaining a scale factor corresponding to the image data, wherein the calibration module determines the coordinate data from the first ellipse parameters, the second ellipse parameters, the geometric parameters of the marker assembly, the intersection point and the scale factor.

9. The system of claim 8, wherein the coordinate data is used to calibrate the source and detector instrument.

10. The system of claim 8, wherein the coordinate data include three source coordinates defining a position of the energy source, three detector position coordinates defining a position of the detector and three detector orientation coordinates defining an orientation of the detector, one of the three detector orientation coordinates being an angle specifying the pitch of the detector.

11. The system of claim 8, wherein the energy source includes at least one of one of an electromagnetic wave source, a particle accelerator and a radionuclide source.

12. The system of claim 8, wherein the energy source includes at least one of an x-ray source, a gamma ray source, an atomic source, a sub-atomic source, and an optical photon source.

13. The system of claim 8, wherein the source and detector instrument includes one of a radiography instrument, a stereography instrument, a bi-plane imaging instrument, a fluoroscopy instrument, a tomosynthesis instrument, and a tomography instrument.

14. The system of claim 8, wherein each of the markers is a metallic sphere.

15. A method of determining coordinate data of a source and detector instrument, the method comprising:

providing a marker assembly having a plurality of markers with a particular three dimensional geometry, wherein the plurality of markers describe a first circle and a second circle that are parallel and lie on a cylinder;

concurrently disposing a target and the plurality of markers within a targeting region;

bombarding the target and the marker assembly in the targeting region with energy packets from at least one energy source;

forming image data of the plurality of markers with a detector, the image data corresponding to a first ellipse associated with a first projection of the first circle onto the detector and a second ellipse associated with a second projection of the second circle onto the detector; and non-iteratively determining coordinate data in a world coordinate system of at least one of the detector and the energy source using the particular geometry of the plurality of markers and the image data, including obtaining first ellipse parameters that describe the first ellipse and second ellipse parameters that describe the second ellipse, wherein the plurality of markers describe a first circle and a second circle that are parallel and lie on a cylinder, wherein the step of determining coordinate data includes using the first ellipse parameters, the second ellipse parameters and the geometric parameters of the marker assembly to obtain the coordinate data;

determining an intersection point where lines connecting points on the first ellipse to opposite points on the second ellipse intersect;

obtaining a scale factor corresponding to the image data;

providing a detector plane connecting pairs of the markers with parallel lines, and constructing divergent planes each containing the energy source and one of the parallel lines connecting the pairs of markers, the divergent planes and the detector plane intersecting at a convergent point;

determining at least one convergent point from the first and second ellipse parameters and the geometric parameters of the marker assembly; and determining the coordinate data from two or more of the first ellipse parameters, the second ellipse parameters, the geometric parameters of the marker assembly, the scale factor, and at least one convergent point;

wherein the method includes determining a center of each of the first and second circles of markers, a piercing point being a point centrally located between the first and second circles and markers and through which lines pass that each connect a marker on the first circle with a marker on the second circle and/or lines extending parallel to an axis extending through the centers of the first and second circles and through a marker on the first circle and a marker on the second circle.

16. The method of claim 15, further comprising calibrating the source and detector instrument with the coordinate data.

17. The method of claim 15, wherein the step of determining includes determining three source coordinates defining a position of the energy source, three detector position coordinates defining a position of the detector and three detector orientation coordinates defining an orientation of the detector, and determining the pose of the source and detector instrument from the source and detector coordinates.

18. A system for obtaining coordinate data of a source and detector instrument, the system comprising:

a marker assembly having a plurality of markers with a particular three dimensional geometry;

a set of energy sources containing at least one member for bombarding the plurality of markers with energy;

a set of detectors containing at least one member, wherein energy emitted from any one member of the set of energy sources may be detected by at least one member of the set of detectors;

at least one image device for forming image data of the plurality of markers from energy detected by the set of detectors; and a calibration module including at least one equation, for non-iteratively determining, from the particular geometry of the plurality of markers and the image data to determine, in a world coordinate system, coordinate data of at least one of the set of energy sources and the set of detectors, wherein at least one of the number of members of the set of energy sources and the number of members of the set of detectors is greater than one;

wherein the number of members of the set of detectors is greater than one, and wherein the coordinate data include coordinates of the members of the set of detectors with respect to at least one common reference frame, the calibration module cross-calibrating the members of the set of detectors using the coordinates.

19. The system of claim 18, wherein the number of members of the set of energy sources is greater than one, and wherein the coordinate data include position coordinates of the members of the set of energy sources with respect to at least one common reference frame, the calibration module cross-calibrating the members of the set of energy sources using the position coordinates.

20. A marker assembly for calibrating a source and detector system, the marker assembly comprising a first set of at least six markers and a second set of at least six markers, the first set of markers disposed substantially on a first plane, and the second set of markers disposed substantially on a second plane, wherein the first set is arranged uniformly on a first circle and the second set is arranged uniformly on a second circle, the first and second circles being parallel and lying on a cylinder, and wherein all of the markers are disposed in the first and second circles and provide the only elements substantially opaque to radiation, for forming an image.

21. The marker assembly of claim 1, wherein the first set and the second set of markers comprise ball bearings.

22. The system of claim 1, wherein the detector includes a detector plane, wherein pairs of the plurality of markers are connected by parallel lines, and divergent planes each contain the energy source and one of the parallel lines, with the divergent planes and the detector plane intersecting at a convergent point; and wherein the calibration module includes a convergent point module for determining at least one convergent point from the first and second ellipse parameters and the geometric parameters of the marker assembly, whereby data on the at least one convergent point enable coordinate data for calibration of the energy source and/or the detector to be calculated; and wherein the calibration module determines the center of each of the circles of markers, a piercing point being a point centrally located between the first and second circles of markers and through which lines pass that each connect a marker on the first circle with a marker on the second circle, and/or lines extending parallel to an axis extending through a center of the first and second circles, and through a marker on the first circle and a marker on the second circle.

* * * * *